US012797373B2

(12) United States Patent
Clarence-Smith et al.

(10) Patent No.: US 12,797,373 B2
(45) **Date of Patent: *Nov. 17, 2026**

(54) COMBINATION THERAPY FOR A DOPAMINE AGONIST

(71) Applicant: Alto Neuroscience, Inc., Mountain View, CA (US)

(72) Inventors: Kathleen E. Clarence-Smith, Mountain View, CA (US); Thomas N. Chase, Mountain View, CA (US)

(73) Assignee: ALTO NEUROSCIENCE, INC., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/453,621

(22) Filed: Jan. 20, 2026

(65) Prior Publication Data

US 2026/0144776 A1 May 28, 2026

Related U.S. Application Data

(63) Continuation of application No. 19/390,174, filed on Nov. 14, 2025, now Pat. No. 12,648,934, which is a continuation of application No. 19/244,143, filed on Jun. 20, 2025, now Pat. No. 12,521,374, which is a continuation of application No. 16/607,252, filed as application No. PCT/US2018/028885 on Apr. 23, 2018, now abandoned.

(60) Provisional application No. 62/489,016, filed on Apr. 24, 2017.

(51) Int. Cl.
*A61K 31/428* (2006.01)
*A61K 31/4178* (2006.01)
*A61P 1/08* (2006.01)
*A61P 25/24* (2006.01)

(52) U.S. Cl.
CPC ........ *A61K 31/428* (2013.01); *A61K 31/4178* (2013.01); *A61P 1/08* (2018.01); *A61P 25/24* (2018.01)

(58) Field of Classification Search
CPC ........................................................ A61P 25/24
See application file for complete search history.

(56) References Cited

U.S. PATENT DOCUMENTS

| | | | |
|---|---|---|---|
| 5,910,319 | A | 6/1999 | Anderson et al. |
| 5,925,627 | A | 7/1999 | Baker et al. |
| 5,962,494 | A | 10/1999 | Young |
| 6,191,153 | B1 | 2/2001 | Hammer et al. |
| 6,255,329 | B1 | 7/2001 | Maj |
| 6,271,230 | B1 | 8/2001 | Baker et al. |
| 6,620,438 | B2 | 9/2003 | Pairet et al. |
| 6,667,329 | B1 | 12/2003 | Maj |
| 8,877,768 | B2 | 11/2014 | Chase et al. |
| 9,012,447 | B2 | 4/2015 | Hitchcock et al. |
| 9,169,255 | B2 | 10/2015 | Esposito et al. |
| 9,303,045 | B2 | 4/2016 | Hitchcock et al. |
| 9,903,391 | B2 | 2/2018 | Heindl |
| 10,213,494 | B2 | 2/2019 | Schlossmacher et al. |
| 10,799,484 | B2 | 10/2020 | Chase et al. |
| 11,160,809 | B2 | 11/2021 | Chase et al. |
| 11,266,633 | B2 | 3/2022 | Chase et al. |
| 11,318,122 | B2 | 5/2022 | Chase et al. |
| 11,547,700 | B2 | 1/2023 | Chase et al. |
| 11,813,247 | B2 | 11/2023 | Chase et al. |
| 11,813,248 | B2 | 11/2023 | Chase et al. |
| 12,521,374 | B1 | 1/2026 | Clarence-Smith et al. |
| 12,622,895 | B2 | 5/2026 | Chase et al. |
| 12,648,934 | B2 | 6/2026 | Clarence-Smith et al. |
| 2002/0042361 | A1 | 4/2002 | Carlson et al. |
| 2004/0063742 | A1 | 4/2004 | Peters et al. |
| 2005/0272722 | A1 | 12/2005 | Lansbury et al. |
| 2007/0032491 | A1 | 2/2007 | Pineiro |
| 2007/0225279 | A1 | 9/2007 | Rosenzweig-Lipson |
| 2008/0014259 | A1 | 1/2008 | Bozik et al. |
| 2009/0041844 | A1 | 2/2009 | Friedl et al. |
| 2009/0042956 | A1 | 2/2009 | Bozik et al. |
| 2009/0221641 | A1 | 9/2009 | Janssens et al. |
| 2009/0258814 | A1 | 10/2009 | Brady et al. |
| 2009/0291966 | A1 | 11/2009 | Frey et al. |
| 2010/0000983 | A1 | 1/2010 | Babington |
| 2010/0093706 | A1 | 4/2010 | Hauske |
| 2010/0105601 | A2 | 4/2010 | Brady et al. |
| 2011/0034442 | A1 | 2/2011 | Legarda Ibanez |
| 2011/0071135 | A1 | 3/2011 | Chase et al. |

(Continued)

FOREIGN PATENT DOCUMENTS

| | | | |
|---|---|---|---|
| AU | 3675299 | A | 8/1999 |
| AU | 2018201519 | A1 | 3/2018 |

(Continued)

OTHER PUBLICATIONS

Chen et al., "The Changes of qEEG Approximate Entropy during Test of Variables of Attention as a Predictor of Major Depressive Disorder," Brain Sci., 10(11):828 (Nov. 2020), 19 pages. doi: 10.3390/brainsci10110828.

(Continued)

*Primary Examiner* — Jeffrey S Lundgren
*Assistant Examiner* — Eric Tran
(74) *Attorney, Agent, or Firm* — COOLEY LLP

(57) ABSTRACT

The application describes a method of reducing emesis caused by a dopamine agonist in a patient with depression who is treated with a dopamine agonist, comprising administering ondansetron in combination with the dopamine agonist.

28 Claims, No Drawings

(56) References Cited

U.S. PATENT DOCUMENTS

| | | | |
|---|---|---|---|
| 2011/0190356 A1 | 8/2011 | Bozik et al. | |
| 2011/0207776 A1 | 8/2011 | Buntinx | |
| 2012/0282227 A1 | 11/2012 | Katz | |
| 2013/0116215 A1 | 5/2013 | Coma et al. | |
| 2013/0225626 A1* | 8/2013 | Bryson | A61F 13/00063 424/443 |
| 2013/0230569 A1 | 9/2013 | Bozik et al. | |
| 2014/0024644 A1 | 1/2014 | Hitchcock et al. | |
| 2014/0128374 A1 | 5/2014 | Davoren et al. | |
| 2014/0336158 A1 | 11/2014 | Paliwal et al. | |
| 2014/0377329 A1 | 12/2014 | Bryson et al. | |
| 2015/0344474 A1 | 12/2015 | Davoren et al. | |
| 2016/0151299 A1 | 6/2016 | Bryson et al. | |
| 2016/0264597 A1 | 9/2016 | Chytil et al. | |
| 2017/0001987 A1 | 1/2017 | Xie et al. | |
| 2017/0015739 A1 | 1/2017 | Kallunki et al. | |
| 2017/0326127 A1 | 11/2017 | Lee | |
| 2020/0016127 A1 | 1/2020 | Chase et al. | |
| 2020/0147053 A1 | 5/2020 | Chase et al. | |
| 2020/0147097 A1 | 5/2020 | Chase et al. | |
| 2020/0375956 A1 | 12/2020 | Chase et al. | |
| 2020/0375957 A1 | 12/2020 | Chase et al. | |
| 2020/0397761 A1 | 12/2020 | Chase et al. | |
| 2021/0338652 A1 | 11/2021 | Chase et al. | |
| 2021/0393595 A1 | 12/2021 | Chase et al. | |
| 2022/0000854 A1 | 1/2022 | Chase et al. | |
| 2022/0071976 A1 | 3/2022 | Chase et al. | |
| 2022/0160683 A1 | 5/2022 | Chase et al. | |
| 2022/0168281 A1 | 6/2022 | Chase et al. | |
| 2022/0265634 A1 | 8/2022 | Pimstone | |
| 2023/0117508 A1 | 4/2023 | Etkin et al. | |
| 2026/0069573 A1 | 3/2026 | Clarence-Smith et al. | |
| 2026/0256744 A1 | 9/2026 | Clarence-Smith et al. | |

FOREIGN PATENT DOCUMENTS

| | | | |
|---|---|---|---|
| CN | 1375292 | A | 10/2002 |
| CN | 103476372 | A | 12/2013 |
| CN | 108721269 | A | 11/2018 |
| EP | 2508181 | A1 | 10/2012 |
| JP | 2007217432 | A | 8/2007 |
| JP | 2009504748 | A | 2/2009 |
| JP | 2016113441 | A | 6/2016 |
| TW | 201841630 | A | 12/2018 |
| WO | WO-9618395 | A1 | 6/1996 |
| WO | WO-9815277 | A2 | 4/1998 |
| WO | WO-9824438 | A1 | 6/1998 |
| WO | WO-9824446 | A1 | 6/1998 |
| WO | WO-1999048484 | A2 | 9/1999 |
| WO | WO-03051840 | A1 | 6/2003 |
| WO | WO-2004010997 | A1 | 2/2004 |
| WO | WO-2004010999 | A1 | 2/2004 |
| WO | WO-2004084865 | A1 | 10/2004 |
| WO | WO-2005084654 | A2 | 9/2005 |
| WO | WO-2005099702 | A2 | 10/2005 |
| WO | WO-2006069030 | A1 | 6/2006 |
| WO | WO-2007134077 | A2 | 11/2007 |
| WO | WO-2007137071 | | 11/2007 |
| WO | WO-2008129043 | A1 | 10/2008 |
| WO | WO-2008132712 | A2 | 11/2008 |
| WO | WO-2008137692 | A1 | 11/2008 |
| WO | WO-2009006050 | A1 | 1/2009 |
| WO | WO-2009059418 | A1 | 5/2009 |
| WO | WO-2009109990 | A2 | 9/2009 |
| WO | WO-2009145900 | A1 | 12/2009 |
| WO | WO-2011034568 | A1 | 3/2011 |
| WO | WO-2011143721 | A1 | 11/2011 |
| WO | WO-2012022439 | A1 | 2/2012 |
| WO | WO-2012083269 | A1 | 6/2012 |
| WO | WO-2013062762 | A1 | 5/2013 |
| WO | WO-2014039627 | A1 | 3/2014 |
| WO | WO-2014078832 | A1 | 5/2014 |
| WO | WO-2016106135 | A1 | 6/2016 |
| WO | WO-2016122218 | A2 | 8/2016 |
| WO | WO-2016130790 | A1 | 8/2016 |
| WO | WO-2016130796 | A1 | 8/2016 |
| WO | WO-2017049158 | A1 | 3/2017 |
| WO | WO-2018039159 | A1 | 3/2018 |
| WO | WO-2018132712 | A1 | 7/2018 |
| WO | WO-2018183192 | A1 | 10/2018 |
| WO | WO-2018191160 | A1 | 10/2018 |
| WO | WO-2018191408 | A1 | 10/2018 |
| WO | WO-2018200387 | A1 | 11/2018 |
| WO | WO-2018217845 | A1 | 11/2018 |
| WO | WO-2019006050 | A1 | 1/2019 |
| WO | WO-2019010146 | A1 | 1/2019 |
| WO | WO-2024130044 | A1 | 6/2024 |
| WO | WO-2025145022 | A1 | 7/2025 |

OTHER PUBLICATIONS

JP Application No. 2023-179963, Decision for Patent mailed May 12, 2026; Applicant Chase Therapeutics Corp; 1 page.

Maitín et al., “Time Series Analysis Applied to EEG Shows Increased Global Connectivity during Motor Activation Detected in PD Patients Compared to Controls,” Applied Sciences, 11:15 (Dec. 2020), 13 pages. https://dx.doi.org/10.3390/app1101001.

Pappalettera et al., “Analysis of complexity in the EEG activity of Parkinson’s disease patients by means of approximate entropy,” Geroscience, 44(3):1599-1607 (Jun. 2022). doi: 10.1007/s11357-022-00552-0. Epub Mar. 28, 2022.

PCT Application No. PCT/US2025/057847, International Search Report and Written Opinion mailed Apr. 22, 2026, Applicant Alto Neuroscience, Inc.; 14 pages.

Tundo et al., “Efficacy and safety of 24-week pramipexole augmentation in patients with treatment resistant depression. A retrospective cohort study,” Prog Neuropsychopharmacol Biol Psychiatry, 112:110425 (Jan. 2022), 9 pages. doi: 10.1016/j.pnpbp.2021.110425. Epub Aug. 8, 2021.

U.S. Appl. No. 19/390,174, Notice of Allowance mailed Apr. 6, 2026; Inventor Clarence-Smith, Kathleen E. et al.; 10 pages.

U.S. Appl. No. 19/653,745, filed Apr. 21, 2026; Inventor Clarence-Smith, Kathleen E. et al.

Abali et al., “Tropisetron, Ondansetron, and Granisetron for Control of Chemotherapy-Induced Emesis in Turkish Cancer Patients: A Comparison of Efficacy, Side-Effect Profile, and Cost,” Cancer Investigation, 25:135-139 (May 2007).

Akhondzadeh S., et al., “Added Ondansetron for Stable Schizophrenia: a Double Blind, Placebo Controlled Trial,” Schizophrenia Research, Feb. 2009, vol. 107, pp. 206-212.

“Altoprev (Iovastatin),” [prescribing information], Watson Laboratories, Tablets: 20 mg, 40 mg, and 60 mg, approved by the U.S. Food and Drug Administration, 2002, last revised Dec. 2012; [Accessed Jun. 17, 2025, publicly available at URL: https://www.accessdata.fda.gov/drugsatfda_docs/label/2012/021316s028lbl.pdf], 20 pages.

Andrews et al., “The 5-Hydroxytryptamine Receptor Antagonists as Antiemetics: Preclinical Evaluation and Mechanism of Action,” Eur J Cancer, 29A (Suppl. 1):S11-S16 (May 1993).

“Apokyn (apomorphine hydrochloride injection),” [prescribing information], US WorldMeds, LLC, Multi-dose glass cartridges: 30 mg/3 mL (10 mg/mL) for use with a multiple dose pen injector (APOKYN Pen) (3, 16), 2004, last revised Mar. 2017; [Accessed Jun. 17, 2025, publicly available at URL: https://www.accessdata.fda.gov/scripts/cder/daf/index.cfm], 19 pages.

Arnold et al., “Domperidone is Superior to Ondansetron in Acute Apomorphine Challenge in Previously Untreated Parkinsonian Patients—A Double Blind Study,” Parkinsonism & Related Disorders, 3(4):191-193 (Dec. 1997).

AU Application No. 2024204167, Examination Report No. 1 mailed Aug. 11, 2025; Applicant Chase Therapeutics Corporation; 3 pages.

AU Application No. 2024204179, Examination Report mailed Aug. 14, 2025; Applicant Chase Therapeutics Corporation; 3 pages.

Bailey et al., “The 5-HT3 antagonist ondansetron reduces gastrointestinal side effects induced by a specific serotonin re-uptake inhibitor in man,” Journal of Psychopharmacology, 9(2):137-141 (Jan. 1995).

(56) References Cited

OTHER PUBLICATIONS

Bar-On et al., "Statins reduce neuronal a-synuclein aggregation in vivo models of Parkinson's disease," J Neurochem., 105:1656-1667 (Jun. 2008).
Barone et al., "Pramipexole for the treatment of depressive symptoms in patients with Parkinson's disease: a randomised, double-blind, placebo-controlled trial," Lancet Neurol, 9(6):573-580 (Jun. 2010).
Barone., "Treatment of depressive symptoms in Parkinson's disease", European Journal of Neurology, 18 (Suppl. 1):11-15 (Mar. 2011).
BCRenalagency, "Restless Leg Syndrome", Nov. 26, 2012 (Nov. 26, 2012), [Retrieved from the Internet on Feb. 11, 2020 from https://www.google.com/search?q=inurl%3Ahttp%3A%2F/02Fwww.bcrenalagency.ca%2Fresourcegallery%2FDocuments%2FSymptom-ManagementProtocolRestlessLegSyndrome1.pdf&rlz=1C1SQJLenUS861US861&oq=inurl%3Ahttp%3A%2F%2Fwww.bcrenalagency.ca%2Fresourcegallery-%2FDocuments%2FSymptomManagementProtocolRestlessLegSyndromel.pdf&aqs=chrome..69i57j69i58.9206j0j7&sourceid=chrome&ie=UTF-8&as_qdr=y15], 12 pages.
Blaine, "Acute severe depression following peri-operative ondansetron," S Afr Med J., 87(8):1013-4 (Aug. 1997).
Bétry et al., "Role of 5-HT3 Receptors in the Antidepressant Response," Pharmaceuticals, 4:603-629 (Apr. 2011).
Chambers D.J. et al. "Parkinson's disease", BJA Education, Sep. 2016, 17(4), pp. 145-149.
Chau et al., "Pramipexole Reduces Phosphorylation of alpha-Synuclein at Seine-129," Journal of Molecular Neuroscience, 51(2):573-580 (Oct. 2013).
Chen et al., "Pharmacologic Safety Concerns in Parkinson's Disease: Facts and Insights," International Journal of Neuroscience, 121 (Suppl 2):45-52 (Apr. 2011).
Clark, L.N. et al., "Mutations in the glucocerebrosidase gene are associated with early-onset Parkinson disease" Neurology, 69(12):1270-1277 (Sep. 2007).
CN Application No. 2018800330262, First Office Action and Search Report mailed Apr. 24, 2022, with English translation; Applicant Chase Therapeutics Corporation; 14 total pages.
CN Application No. 2018800330262, Rejection decision for mailed Dec. 21, 2022, with English translation; Applicant Chase Therapeutics Corporation; 7 total pages.
CN Application No. 201880050660.7, Communication mailed Jul. 2, 2021; Applicant Chase Therapeutics Corp; 1 page.
CN Application No. 201880050660.7, Decision of Rejection dated Mar. 22, 2022, with English translation; Applicant Chase Therapeutics Corporation; 12 total pages.
CN Application No. 201980077431.9, First Office Action and Search Repor mailed Apr. 14, 2023, with English translation; Applicant Chase Therapeutics Corporation; 13 total pages.
CN Application No. 201980091133.5, First Office Action and Search Report mailed Jun. 29, 2023, with English translation; Applicant Chase Therapeutics Corp; 18 pages.
Corrigan et al., "Comparison of pramipexole, fluoxetine, and placebo in patients with major depression," Depression and Anxiety, 11(2):58-65 (Feb. 2000).
Costall et al., "5-HT3 receptors," Curr Drug Targets CNS Neurol Disord, 3(1):27-37 (Jan. 2004).
Curran et al., "Aprepitant: A Review of its Use in the Prevention of Nausea and Vomiting," Drugs, 69(13):1853-1878 (Sep. 2009).
Curriculum Vitae of Kathleen E. (Biziere) Clarence-Smith, M.C., Ph.D., 20 pages. [No date provided].
Cusin et al., "A randomized, double-blind, placebo-controlled trial of pramipexole augmentation in treatment-resistant depressive disorder," J. Clin Psychiatry, 74(7):e636-e641 (Jul. 2013).
De Sousa et al., "Challenging Treatment-Resistant Major Depressive Disorder: A Roadmap for Improved Therapeutics," Current Neuropharmacology, 13:616-635 (Sep. 2015).
Declaration of Dr. Kathleen E. Clarence-Smith dated Aug. 1, 2023 and filed Apr. 23, 2018 for U.S. Appl. No. 18/790,791, 4 pages.
Declaration of Dr. Kathleen E. Clarence-Smith dated Jun. 16, 2025, 14 pages.
Dell'Osso et al., "Assessing efficacy/effectiveness and safety tolerability profiles of adjunctive pramipexole in bipolar depression: acute versus long-term data," International Clinical Psychopharmacology, 28(6):297-304 (Nov. 2013).
Diemunsch P et al: "Neurokinin-1 receptor antagonists in the prevention of postoperative nausea and vomiting", British Journal of Anaesthesia vol. 103, No. 1, Jul. 1, 2009 (Jul. 1, 2009), pp. 7-13, ISSN: 0007-0912, DOI: 10.1093/BJA/AEP125 [retrieved on May 19, 2009].
EA Application No. 201992284, Official Action dated Mar. 31, 2021, with English translation; Applicant Chase Therapeutics Corporation; 6 total pages.
EA Application No. 202090180, Communication dated Jun. 6, 2022, with English translation; Applicant Chase Therapeutics Corporation; 5 total pages.
EA Application No. 202090180, Communication dated Nov. 16, 2021, with English translation; Applicant Chase Therapeutics Corporation; 19 total pages.
"Emend (aprepitant)," [prescribing information], Merck & Co., Inc., Capsules: 40mg, 80mg, 125 mg, approved by the U.S. Food and Drug Administration, 2010, last revised Mar. 2010; [Accessed Jun. 17, 2025, publicly available at URL: https://www.accessdata.fda.gov/drugsatfda_docs/label/2018/022023s017lbl.pdf], 28 pages.
Endrenyi et al., "Metrics for the Evaluation of Bioequivalence of Modified-Release Formulations," The AAPS Journal, 14(4):813-819 (Aug. 2012).
EP Application No. 18 824 955.1, Examination Report dated Oct. 6, 2022; Applicant Chase Therapeutics Corporation; 6 pages.
EP Application No. 18777889, Communication dated Nov. 27, 2023; Applicant Chase Therapeutics Corporation; 5 pages.
EP Application No. 18777889.9, Extended European Search Report dated Nov. 23, 2020; Applicant Chase Therapeutics Corporation; 9 pages.
EP Application No. 18777889.9, Office Action mailed Apr. 30, 2025; Applicant Chase Therapeutics Corporation; 5 pages.
EP Application No. 18784304.0, Extended European Search Report dated Feb. 8, 2021; Applicant Chase Therapeutics Corporation; 7 pages.
EP Application No. 18784304.0, Office Action for European mailed Nov. 29, 2022; Applicant Chase Therapeutics Corporation; 5 pages.
EP Application No. 18784304.0, Office Action mailed Aug. 5, 2024; Applicant Chase Therapeutics Corporation; 6 pages.
EP Application No. 18785191, Extended European Search Report dated Oct. 29, 2020; Applicant Chase Therapeutics Corporation; 10 pages.
EP Application No. 18785191.0, Decision to grant for European mailed Jun. 27, 2024; Applicant Chase Therapeutics Corporation; 2 pages.
EP Application No. 18790791, Communication dated Dec. 22, 2020; Applicant Chase Therapeutics Corporation; 8 pages.
EP Application No. 18790791, Communication dated May 31, 2023; Applicant Chase Therapeutics Corporation; 8 pages.
EP Application No. 18790791.0, Extended European Search Report dated Dec. 20, 2022; Applicant Chase Therapeutics Corporation; 7 pages.
EP Application No. 18790791.0, Office Action mailed Mar. 19, 2025; Applicant Chase Therapeutics Corporation; 5 pages.
EP Application No. 18824955.1, Communication mailed Oct. 29, 2021; Applicant Chase Therapeutics Corporation; 6 pages.
EP Application No. 18824955.1, Extended European Search Report dated Feb. 19, 2021; Applicant Chase Therapeutics Corporation; 9 pages.
EP Application No. 19864237.3, Extended European Search Report mailed Jun. 7, 2022; Applicant Chase Therapeutics Corporation; 10 pages.
EP Application No. 19864237.3, Office Action for European mailed Sep. 26, 2024; Applicant Chase Therapeutics Corporation; 5 pages.
EP Application No. 19905532.8, Extended European Search Report mailed Oct. 6, 2022; Applicant Chase Therapeutics Corporation; 10 pages.

(56) References Cited

OTHER PUBLICATIONS

EP Application No. 19905532.8, Office Action for European mailed Nov. 13, 2024; Applicant Chase Therapeutics Corporation; Applicant Chase Therapeutics Corporation; 5 pages.
EP Application No. 24189957.4, Extended European Search Report for European mailed Jan. 20, 2025, Applicant Chase Therapeutics Corporation, 9 pages.
Eser et al., "Depression and Parkinson's disease: prevalence, temporal relationship, and determinants," Turk Med J Sci, 47:499-503 (Apr. 2017).
Fava et al., "Double-blind, Placebo-controlled Trial of Pramipexole Augmentation in Treatment-resistant Major Depressive Disorder," ACNP 51st Annual Meeting, Dec. 2-6, 2012, vol. 38, Supp. 1, pp. S441-S442, Abstract No. W211, 2 pages.
Fawcett et al., "Clinical Experience with High-Dosage Pramipexole in Patients with Treatment-Resistant Depressive Episodes in Unipolar and Bipolar Depression," Am J Psychiatry, 173(2):107-111 (Feb. 2016).
Goldberg et al., "Preliminary Randomized, Double-Blind, Placebo-Controlled Trial of Pramipexole Added to Mood Stabilizers for Treatment-Resistant Bipolar Depression," Am J Psychiatry, 161(3):564-566 (Mar. 2004).
Hawke's Bay Health, "Primary Care Prescribing Advice," Apr. 2012, 2 pages.
Hobson, D. E. et al., "Ropinirole and Pramipexole, the New Agonists," Can. J. Neurol. Sci., 26(S2):S27-S33 (Aug. 1999).
Hoffman et al., "Ondansetron and metformin-induced gastrointestinal side effects," Am J Ther 10(6):447-51 (Nov. 2003). doi: 10.1097/00045391-200311000-00012.
Hori et al., "The Efficacy of Pramipexole, a Dopamine Receptor Agonist, as an Adjunctive Treatment in Treatment-Resistant Depression: An Open-Label Trial," The Scientific World Journal, 2012:372474 (Aug. 2012). doi: 10.1100/2012/372474, 9 pages.
IL Application No. 271464, Office Action dated Jun. 12, 2022; Applicant Chase Therapeutics Corporation; 6 pages.
IN Application No. 201917047075, Communication dated Oct. 13, 2020; Applicant Chase Therapeutics Corporation; 5 pages.
IN Application No. 202017003521, Communication dated Oct. 27, 2022; Applicant Chase Therapeutics Corporation; 2 pages.
IN Application No. 202017003521, First Examination Report dated Mar. 24, 2021; Applicant Chase Therapeutics Corporation; 5 pages.
Inoue et al., "Pramipexole for stage 2 treatment-resistant major depression: An open study," Progress in Neuro-Psychopharmacology & Biological Psychiatry, 34:1446-1449 (Dec. 2010).
Jhee et al., "Centrally acting antiemetics mitigate nausea and vomiting in patients with Alzheimer's disease who receive rivastigmine," Clinical Neuropharmacology, 25(2):122-123 (Mar.-Apr. 2002).
JP Application No. 2019-554412, Decision of Refusal mailed Nov. 1, 2022; Applicant Chase Therapeutics Corporation, with English translation; 8 total pages.
JP Application No. 2019-554412, Notice of Reasons for Refusal mailed Dec. 14, 2021; Applicant Chase Therapeutics Corporation, with English translation, 11 pages.
JP Application No. 2019-554412, Notice of Reasons for Refusal mailed Jun. 25, 2024, with English translation, Applicant Chase Therapeutics Corporation; 6 total pages.
JP Application No. 2019-554412, Search Report by Registered Search Organization mailed Nov. 17, 2021, with English translation; Applicant Chase Therapeutics Corporation; 59 total pages.
JP Application No. 2019-555469, Decision to Grant a Patent for Japanese mailed Mar. 28, 2023, with English translation; Applicant Chase Therapeutics Corporation; 5 total pages.
JP Application No. 2019-555469, Notice of Reasons for Refusal for Japanese mailed Feb. 16, 2022, with English translation; Applicant Chase Therapeutics Corporation, 9 total pages.
JP Application No. 2019-555469, Notice of Reasons for Refusal mailed Nov. 8, 2022; Applicant Chase Therapeutics Corporation, with English translation; 6 pages.
JP Application No. 2019-557617, Decision of Refusal mailed Jun. 20, 2023; Applicant Chase Therapeutics Corporation, with English translation; 6 total pages.
JP Application No. 2019-557617, Decision to Grant a Patent mailed Nov. 14, 2023, with English translation; Applicant Chase Therapeutics Corporation; 6 total pages.
JP Application No. 2019-557617, Notice of Reasons for Refusal mailed Jan. 11, 2022; Applicant Chase Therapeutics Corporation, with English translation; 8 total pages.
JP Application No. 2019-557617, Notice of Reasons for Refusal mailed Oct. 11, 2022; Applicant Chase Therapeutics Corporation, with English translation; 8 total pages.
JP Application No. 2019-557617, Search Report mailed Dec. 28, 2021; Applicant Chase Therapeutics Corporation; 23 pages.
JP Application No. 2019-572041, Decision to Grant a Patent for Japanese mailed Sep. 13, 2022, with English translation; Applicant Chase Therapeutics Corporation; 5 total pages.
JP Application No. 2019-572041, Notice of Reasons for Rejection dated Feb. 15, 2022, with English translation; Applicant Chase Therapeutics Corporation; 8 total pages.
JP Application No. 2019-572041, Search Report by Registered Search Organization mailed Feb. 7, 2022, with English translation; Applicant Chase Therapeutics Corporation; 47 total pages.
JP Application No. 2021-536745, Decision of Refusal mailed Apr. 26, 2024, with English translation, Applicant Chase Therapeutics Corporation; 2 total pages.
JP Application No. 2021-536745, Notice of Reasons for Refusal for Japanese mailed Sep. 5, 2023, with English translation; Applicant Chase Therapeutics Corporation; 9 total pages.
JP Application No. 2021-536745, Search Report by Registered Search Organization mailed Aug. 16, 2023, with English translation; Applicant Chase Therapeutics Corporation; 44 total pages.
JP Application No. 2021-537793, Decision of Refusal mailed Apr. 2, 2024, with English translation; Applicant Chase Therapeutics Corporation; 2 total pages.
JP Application No. 2021-537793, Notice of Reasons for Refusal mailed Sep. 8, 2023, with English translation; Applicant Chase Therapeutics Corporation; 8 total pages.
JP Application No. 2021-537793, Search Report by Registered Search Organization mailed Aug. 16, 2023, with English translation; Applicant Chase Therapeutics Corporation; 39 total pages.
JP Application No. 2023-030614, Decision of Refusal mailed Oct. 29, 2024, with English translation; Applicant Chase Therapeutics Corporation; 2 total pages.
JP Application No. 2023-030614, Decision to Grant a Patent mailed Jun. 10, 2025, with English translation; Applicant Chase Therapeutics Corporation, 5 total pages.
JP Application No. 2023-030614, Notice of Reasons for Refusal mailed Jan. 16, 2024, with English translation; Applicant Chase Therapeutics Corporation; 14 total pages.
JP Application No. 2023-179963, Notice for Reasons of Refusal mailed Aug. 26, 2025, with English translation; Applicant Chase Therapeutics Corporation, 6 total pages.
JP Application No. 2023-179963, Notice for Reasons of Refusal mailed Nov. 26, 2024; Applicant Chase Therapeutics Corp, with English translation, 10 pages.
JP Application No. No. 2019-554412, Notice of Reasons for Refusal mailed Mar. 12, 2024, with English translation; Applicant Chase Therapeutics Corporation; 38 total pages.
Kast et al., "Cancer chemotherapy and cachexia: mirtazapine and olanzapine are 5-HT3 antagonists with good antinausea effects", European Journal of Cancer Care, 16(4):351-354 (Jul.-Aug. 2007).
Kleeblat et al., "Efficacy of off-label augmentation in unipolar depression: A systematic review of the evidence," European Neuropsychopharmacology, 27:423-441 (Apr. 2017).
Koo et al., "Manufacturing process considerations for fixed-dose combination drug products," Apr. 1, 2010, American Pharmaceutical Review, 6 pages. [Retrieved from the Internet on Jul. 31, 2025 at https://www.americanpharmaceuticalreview.com/Featured-Articles/117118-Manufacturing-Process-Considerations-for-Fixed-Dose-Combination-Drug-Products/].

(56) References Cited

OTHER PUBLICATIONS

Koob et al., "Lovastatin ameliorates-synuclein accumulation and oxidation in transgenic mouse models of synucleinopathies," Experimental Neurology, vol. 221, pp. 267-274 (Feb. 2009).
KR Application No. 10-2019-7031743, Notice of Final Rejection mailed Jul. 3, 2023, with English translation; Applicant Chase Therapeutics Corporation; 8 total pages.
KR Application No. 10-2019-7031743, Request for the Submission of an Opinion for Korean mailed Oct. 5, 2022, with English translation; Applicant Chase Therapeutics Corporation; 11 total pages.
KR Application No. 10-2019-7031743, Written Decision on Registration mailed Nov. 6, 2023, with English translation; Applicant Chase Therapeutics Corporation, 5 total pages.
KR Application No. 10-2019-7034504, Notice of Final Rejection dated Aug. 1, 2024; Applicant Chase Therapeutics Corporation, with English translation; 9 total pages.
KR Application No. 10-2019-7034504, Request for the Submission of an Opinion mailed Jan. 3, 2023; Applicant Chase Therapeutics Corporation, with English translation; 9 pages.
KR Application No. 10-2020-7002891, Notice of Final Rejection for Korean mailed Dec. 11, 2024, with English translation; Applicant Chase Therapeutics Corporation; 14 total pages.
KR Application No. 10-2020-7002891, Notice of Final Rejection for Korean mailed Jul. 9, 2024, with English translation; Applicant Chase Therapeutics Corporation; 14 total pages.
KR Application No. 10-2020-7002891, Request for the Submission of an Opinion mailed Jul. 14, 2023, with English translation; Applicant Chase Therapeutics Corporation, 9 total pages.
KR Application No. 10-2021-7012445, Request for the Submission of an Opinion mailed Feb. 20, 2025, English translation; Applicant Chase Therapeutics Corporation; 7 total pages.
KR Application No. 10-2021-7023839, Request for the Submission of an Opinion mailed Feb. 20, 2025, with English translation; Applicant Chase Therapeutics Corporation; 17 total pages.
KR Application No. 10-2023-7033748, Notice of Final Rejection for Korean mailed Feb. 3, 2025, with English translation; Applicant Chase Therapeutics Corporation; 9 total pages.
KR Application No. 10-2023-7033748, Request for the Submission of an Opinion mailed Mar. 4, 2024, with English translation; Applicant Chase Therapeutics Corporation; 11 total pages.
Kramer et al., "Demonstration of the Efficacy and Safety of a Novel Substance P(NK1) Receptor Agonist in Major Depression," Neuropsychopharmacology, 29:385-392 (Feb. 2004).
Kramer et al., "Distinct mechanism for antidepressant activity by blockade of central substance P receptors," Science, 281:1640-1645 (Sep. 1998).
Kuntz, Anhedonia in Major Depressive Disorder: Understanding Patient Burden, Psychiatric Times, Sep. 10, 2023, 2 pages. [Retrieved from the internet on Feb. 12, 2025 at URL: https://www.psychiatrictimes.com/view/anhedonia-in-major-depressive-disorderunderstanding-patient-burden].
"Kynmobi (apomorphine hydrochloride)," [prescribing information], Sumitomo Pharma AM, Sublingual Film: 10 mg, 15 mg, 20 mg, 25 mg, and 30 mg, approved by the US Food and Drug Administration, 2020, last revised Sep. 2022; [Accessed on Jun. 17, 2025, publicly available at URL: https://www.accessdata.fda.gov/scripts/cder/daf/index.cfm], 35 pages.
Lara, D. R. et al., "Ondansetron Rather than Metoclopramide for Bupropion-Induced Nausea," The Canadian Journal of Psychiatry, 46(4):371 (Apr. 2001), 1 page.
Makiguchi et al., "Mirtazapine-Induced Restless Legs Syndrome Treated with Pramipexole," The Journal of Neuropsychiatry and Clinical Neuroscience, 27(1):e76 (Jan. 2015), 1 page.
Marsh, "Depression and Parkinson's Disease: Current Knowledge," Curr Neurol Neurosci Rep., 13(12):1-17 (Dec. 2013).
"Mirapex, (pramipexole dihydrochloride," [prescribing information], Boehringer Ingelheim, Tablets: 0.125 mg, 0.25 mg, 0.5 mg, 0.75 mg, 1 mg, and 1.5 mg, approved by the US Food and Drug Administration, 1997, last revised Jul. 2016; [Accessed on Jun. 17, 2025, publicly available at URL: https://www.accessdata.fda.gov/scripts/cder/daf/index.cfm], 28 pages.
Montastruc et al., "Does Fluoxetine Aggravate Parkinson's Disease? A Pilot Prospective Study," Movement Disorders, 10(3):355-357 (May-Jun. 1995).
Munchau, A., "Pharmacological treatment of Parkinson's disease," Postgrad Med J., Aug. 2000, vol. 76602-610.
MX Application No. MX/a/2019/015150, Office Action dated Feb. 21, 2022; Applicant Chase Therapeutics Corporation; 6 pages.
MX Application No. MX/a/2019/015150, Office Action dated Sep. 29, 2021; Applicant Chase Therapeutics Corporation; 9 pages.
[No Author Listed], "Management of Restless Leg Syndrome in Patients with Chronic Kidney Disease," Aug. 31, 2017, 7 pages. [Retrieved from the Internet on Oct. 29, 2025 at http:// www.bcrenal.ca/resorce-gallary/Documents/].
Nomura et al., "Prevalence and Clinical Characteristics of Restless Legs Syndrome in Japanese Patients with Parkinson's Disease," Movement Disorders, 21(3):380-384 (Mar. 2006).
Oren, "Dysphoria after treatment with ondansetron," Am J Psychiatry, 152(7):1101 (Jul. 1995). doi: 10.1176/ajp.152.7.1101a, 1 page.
Pae, "Pramipexole augmentation in treatment-resistant major depressive disorder," Expert Review of Neurotherapeutics, 14(1):5-8 (Jan. 2014).
PCT Application No. PCT/US2018/024344, International Preliminary Report on Patentability mailed Oct. 10, 2019; Applicant Chase Therapeutics Corporation; 9 pages.
PCT Application No. PCT/US2018/024344, International Search Report and Written Opinion mailed Aug. 8, 2018; Applicant Chase Therapeutics Corporation; 17 pages.
PCT Application No. PCT/US2018/026699, International Preliminary Report on Patentability mailed Oct. 24, 2019; Applicant Chase Therapeutics Corporation; 8 pages.
PCT Application No. PCT/US2018/026699, International Search Report and Written Opinion mailed Jun. 18, 2018; Applicant Chase Therapeutics Corporation; 11 pages.
PCT Application No. PCT/US2018/027155, International Preliminary Report on Patentability mailed Oct. 24, 2019; Applicant Chase Therapeutics Corporation; 10 pages.
PCT Application No. PCT/US2018/027155, International Search Report and Written Opinion mailed Jun. 20, 2018; Applicant Chase Therapeutics Corporation; 14 pages.
PCT Application No. PCT/US2018/028885, International Preliminary Report on Patentability mailed Nov. 7, 2019; Applicant Chase Therapeutics Corporation; 5 pages.
PCT Application No. PCT/US2018/028885, International Search Report mailed Jul. 19, 2018; Applicant Chase Therapeutics Corporation; 11 pages.
PCT Application No. PCT/US2018/039883, International Preliminary Report on Patentability for mailed Jan. 9, 2020; Applicant Chase Therapeutics Corporation, 11 pages.
PCT Application No. PCT/US2018/039883, International Search Report and Written Opinion mailed Sep. 11, 2018; Applicant Chase Therapeutics Corporation; 17 pages.
PCT Application No. PCT/US2018/24344, Invitation to Pay Additional Fees mailed Jun. 4, 2018; Applicant Chase Therapeutics Corporation; 2 pages.
PCT Application No. PCT/US2019/052705, International Preliminary Report on Patentability mailed Apr. 8, 2021; Applicant Chase Therapeutics Corporation, 8 pages.
PCT Application No. PCT/US2019/052705, International Search Report and Written Opinion mailed Dec. 12, 2019; Applicant Chase Therapeutics Corporation; 14 pages.
PCT Application No. PCT/US2019/052849, International Preliminary Report on Patentability mailed Apr. 8, 2021; Applicant Chase Therapeutics Corporation; 8 pages.
PCT Application No. PCT/US2019/052849, International Search Report and Written Opinion mailed Feb. 4, 2020; Applicant Chase Therapeutics Corporation; 14 pages.
PCT Application No. PCT/US2019/052849, Invitation to Pay Additional Fees mailed Nov. 22, 2019; Applicant Chase Therapeutics Corporation; 2 pages.

(56) References Cited

OTHER PUBLICATIONS

PCT Application No. PCT/US2019/064112, International Preliminary Report on Patentability mailed Jul. 8, 2021; Chase Therapeutics Corporation; 8 pages.
PCT Application No. PCT/US2019/064112, International Search Report and Written Opinion mailed Feb. 10, 2020; Applicant Chase Therapeutics Corporation; 13 pages.
PCT Application No. PCT/US2019/065973, International Preliminary Report on Patentability mailed Jul. 8, 2021; Applicant Chase Therapeutics Corporation; 9 pages.
PCT Application No. PCT/US2019/065973, International Search Report and Written Opinion mailed Feb. 27, 2020; Applicant Chase Therapeutics Corporation; 14 pages.
PCT Application No. PCT/US2024/062080, International Search Report and Written Opinion mailed Apr. 8, 2025; Applicant Chase Therapeutics Corporation; 32 pages.
PCT Application No. PCT/US2024/062080, Invitation to Pay Additional Fees mailed Feb. 14, 2025; Applicant Chase Therapeutics Corporation; 4 pages.
PCT Application No. PCT/US2025/033051, International Search Report and Written Opinion mailed Oct. 22, 2025; Applicant Chase Therapeutics Corporation; 16 pages.
Piercy, "Pharmacology of pramipexole, a dopamine-D3-preferring agonist, useful in treating Parkinson's Disease," Clinical Neuropharmacology, 21(3):141-151 (May-Jun. 1998).
Poon et al., "Pharmacological Approaches for Treatment-resistant Bipolar Disorder," Current Neuropharmacology, 13(5):592-604 (Sep. 2015).
PubChem, Compound 166589, "pramipexole dihydrochloride monohydrate," [compound database record], National Center for Biotechnology Information (NCBI), record created Jun. 24, 2005, modified Dec. 13, 2025. [Accessed Dec. 15, 2025, publicly available at URL: https://pubchem.ncbi.nlm.nih.gov/compound/Pramipexole-dihydrochloride-monohydrate], 33 pages.
Reichmann, "Pramipexole in Routine Clinical Practice", CNS Drug, vol. 17, pp. 965-973, (Aug. 2003).
"Requip (ropinirole)," [prescribing information], GlaxoSmithKline, Tablets: 0.25 mg, 0.5 mg, 1 mg, 2 mg, 3 mg, 4 mg, and 5 mg, approved by the US Food and Drug Administration, 1997, last revised Aug. 2014; [Accessed Aug. 28, 2025, publicly available at URL: https://www.accessdata.fda.gov/drugsatfda_docs/label/2014/020658s024s026s027s030s032lbl.pdf], 43 pages.
Rupniak & Kramer, "NK1 receptor antagonists for depression: Why a validated concept was abandoned," Journal of Affective Disorders, 223:121-12 (Jan. 2017).
Samuels et al., "Comparison of pramipexole with and without domperidone co-administration on alertness, autonomic, and endocrine functions in health volunteers," British Journal of Clinical Pharmacology, 64(5):591-602 (Jun. 2007).
Santiago et al., Depressive-like behaviors alterations induced by intranigral MPTP, 6-OHDA, LPS and rotenone models of Parkinson's disease are predominantly associated with serotonin and dopamine, Progress in Neuro-Psychopharmacology & Biological Psychiatry, vol. 34, pp. 1104-1114 (Jun. 2010).
Schapira et al., "Pramipexole in patients with early Parkinson's disease (PROUD): a randomized delayed-start trial," Lancet Neurol, 12:747-755 (Aug. 2013).
Schneider et al., "Dopamine Autoreceptor Agonists: Resolution and Pharmacological Activity of 2,6-Diaminotetrahydrobenxothiazole and an Aminothiazole Analogue of Apomorphine," J. Med. Chem., 30(3):494-498 (Mar. 1987).
Setron Tablet, Oct. 2014. [Accessed Jul. 1, 2022 at URL: https://www.tabletwise.net/setron-tablet], 14 pages.
Sienaert et al., "Evidence-based treatment strategies for treatment-resistant bipolar depression: a systematic review," Bipolar Disorders, 15(1):61-69 (Jan. 2013).
Simonetto et al., "Acute Akinesia, an unusual complication in Parkinson's Disease: a case report," Neurol Sci, 29:181-183 (Jan. 2008).
Smith et al., "5HT3 receptor antagonists for the treatment of nausea/vomiting," Ann Palliat. Med, 1(2):115-120 (Apr. 2012).
Spencer et al., "Prescribing antiemetics for patients with Parkinson's," Prescriber. 22(18):48-49 (Sep. 2011).
Stimmel et al., "Mirtazapine: An Antidepressant with Noradrenergic and Specific Serotonergic Effects," Pharmacotherapy, 17(1):10-21 (Jan. 2012).
Szegedi et al., "Pramipexole, a Dopamine Agonist, in Major Depression: Antidepressant Effects and Tolerability in an Open-Label Study with Multiple Doses," Clinical Neuropharmacology, 20 (Suppl. 1):S36-S45 (Aug. 1997).
Tondo et al., "Options for pharmacological treatment of refractory bipolar depression," Curr Psychiatry Rep., 16(2):431 (Feb. 2014). doi: 10.1007/s11920-013-0431-y, 7 pages.
TW Application No. 107122579, Communication dated Sep. 29, 2022, with English translation; Applicant Chase Therapeutics Corporation; 9 total pages.
TW Application No. 107122579, Search Report dated Feb. 15, 2022; Applicant Chase Therapeutics Corporation; 1 page.
Ubhi et al., "Fluoxetine ameliorates behavioral and neuropathological deficits in a transgenic model mouse of alpha-synucleinopathy," Experimental Neurology, 234(2):405-416 (Dec. 2012).
U.S. Appl. No. 16/497,006, Non-Final Office Action mailed May 1, 2020; Inventor Chase, Thomas N. et al.; 6 pages.
U.S. Appl. No. 16/604,468, Non-Final Office Action mailed Feb. 9, 2021; Inventor Chase, Thomas N. et al; 9 pages.
U.S. Appl. No. 16/604,689, Non-Final Office Action mailed Apr. 15, 2021; Inventor Chase, Thomas N. et al; 15 pages.
U.S. Appl. No. 16/607,252, Examiner Interview Summary Nov. 7, 2025, Inventor Chase, Thomas N. et al.; 3 pages.
U.S. Appl. No. 16/607,252, Final Office Action mailed Feb. 26, 2024; Inventor Chase, Thomas N. et al.; 22 pages.
U.S. Appl. No. 16/607,252, Final Office Action mailed Jul. 12, 2022; Inventor Chase, Thomas N. et al.; 28 pages.
U.S. Appl. No. 16/607,252, Non-Final Office Action mailed Dec. 14, 2021; Inventor Chase, Thomas N. et al.; 20 pages.
U.S. Appl. No. 16/607,252, Non-Final Office Action mailed Dec. 20, 2024; Inventor Chase, Thomas N. et al.; 20 pages.
U.S. Appl. No. 16/607,252, Non-Final Office Action mailed May 3, 2023; Inventor Chase, Thomas N. et al.; 20 pages.
U.S. Appl. No. 16/607,252, Non-Final Office Action mailed Sep. 8, 2025; Inventor Chase, Thomas N. et al.; 26 pages.
U.S. Appl. No. 16/607,252, Restriction Requirement mailed Jul. 15, 2021; Inventor Chase, Thomas N. et al.; 9 pages.
U.S. Appl. No. 17/006,963, Final Office Action mailed Nov. 12, 2021; Inventor Chase, Thomas N. et al; 5 pages.
U.S. Appl. No. 17/006,963, Non-Final Office Action mailed Apr. 2, 2021; Inventor Chase, Thomas N. et al; 7 pages.
U.S. Appl. No. 17/006,963, Non-Final Office Action mailed Jul. 23, 2021; Inventor Chase, Thomas N. et al; 6 pages.
U.S. Appl. No. 17/279,644, Final Office Action mailed Sep. 29, 2024; Inventor Chase, Thomas N. et al; 18 pages.
U.S. Appl. No. 17/279,644, Non-Final Office Action mailed Jul. 1, 2025; Inventor Chase, Thomas N. et al; 18 pages.
U.S. Appl. No. 17/279,705, Final Office Action mailed Nov. 13, 2024; Inventor Chase, Thomas N. et al; 16 pages.
U.S. Appl. No. 17/279,705, Non-Final Office Action mailed Feb. 15, 2024; Inventor Chase, Thomas N. et al; 17 pages.
U.S. Appl. No. 17/279,705, Notice of Allowance mailed Nov. 7, 2025; Inventor Chase, Thomas N. et al; 9 pages.
U.S. Appl. No. 17/291,497, Non-Final Office Action mailed Sep. 29, 2024; Inventor Chase, Thomas N. et al; 18 pages.
U.S. Appl. No. 17/671,016, Non-Final Office Action mailed Mar. 31, 2023; Inventor Chase, Thomas N. et al; 6 pages.
U.S. Appl. No. 17/671,127, Non-Final Office Action mailed Mar. 17, 2023; Inventor Chase, Thomas N. et al; 6 pages.
U.S. Appl. No. 19/244,143, Examiner Interview Summary mailed Sep. 8, 2025; Inventor Clarence-Smith, E. et al.; 3 pages.
U.S. Appl. No. 19/244,143, Examiner Interview Summary Record for mailed Aug. 25, 2025; Inventor Clarence-Smith, E. et al; 2 pages.
U.S. Appl. No. 19/244,143, Final Office Action mailed Oct. 31, 2025; Inventor Clarence-Smith, E. et al; 20 pages.

(56) References Cited

OTHER PUBLICATIONS

U.S. Appl. No. 19/244,143, Non-Final Office Action for mailed Aug. 25, 2025; Inventor Clarence-Smith, E. et al; 20 pages.
U.S. Appl. No. 19/244,143, Notice of Allowance mailed Dec. 8, 2025; Inventor Smith, Kathleen E. Clarence et al.; 12 pages.
U.S. Appl. No. 19/434,945, filed Dec. 29, 2025; Inventor Chase, Thomas N. et al.
Wagstaff et al., "Once-Weekly Fluoxetine," Drugs, 61(15):2221-8 (Dec. 2001).
Weintraub Daniel et al., "Parkinson's disease—Part 2: Treatment of motor symptoms", Am J Manag Care, Feb. 2008, vol. 14, No. 2, p. S49-S58.
Willner et al., "Reversal of stress-induced anhedonia by the dopamine agonist, pramipexole," Psychopharmacology, 115:454-462 (Dec. 1994).
Wood, "Clinical review and treatment of select adverse effects of dopamine receptor agonists in Parkinson's disease," Drugs & Aging, 27(4):295-310 (Apr. 2010).
"Zofran (ondansetron hydrochloride)," [prescribing information], GlaxoSmithKline, Tablets: 4 mg and 8 mg, approved by the US Food and Drug Administration, 1991, last revised Oct. 2016; [Accessed on Sep. 25, 2025, publicly available at URL: https://www.accessdata.fda.gov/drugsatfda_docs/label/2016/020103s035_020605s019_020781s019lbl.pdf], 21 pages.
Zoldan et al., "Psychosis in advanced Parkinson's disease: Treatment with ondansetron, a 5-HT3 receptor antagonist," Neurology, 45:1305-1308 (Jul. 1995).
AU Application No. 2018243718, Examination Report dated Jun. 22, 2023; Applicant Chase Therapeutics Corporation; 4 total pages.
AU Application No. 2018243718, Examination Report dated Mar. 15, 2024; Applicant Chase Therapeutics Corporation; 5 total pages.
AU Application No. 2024204179, Examination report No. 2 mailed Jul. 6, 2026; Applicant Alto Neuroscience, Inc.; 2 total pages.
AU Application No. 2024204179, Notice of Acceptance dated Aug. 18, 2026; Applicant Alto Neuroscience, Inc.; 3 Pages.
BR Application No. BR112019020100-9, Examination Report dated Aug. 6, 2024; Applicant Chase Therapeutics Corporation; with machine English translation 6 pages.
BR Application No. BR112019020100-9, Examination Report dated Dec. 9, 2024; Applicant Chase Therapeutics Corporation; with machine English translation 8 pages.
BR Application No. BR112019020100-9, Examination Report dated Jul. 21, 2022; Applicant Chase Therapeutics Corporation; with English translation 6 pages.
CA Application No. 3,058,395, Office Action dated Jan. 30, 2024; Applicant Chase Therapeutics Corporation; 4 total pages.
CA Application No. 3,058,395, Office Action dated Jun. 9, 2023; Applicant Chase Therapeutics Corporation; 6 total pages.
CN Application No. 201880033026.2, Office Action dated May 26, 2026; Chase Therapeutics Corporation; with English translation 13 pages.
CN Application No. 201880036987.9, Office Action dated May 9, 2026; Chase Therapeutics Corporation; with English translation 21 pages.
EP Application No. 18777889, Office Action dated Jul. 23, 2026; Applicant Chase Therapeutics Corporation; 5 pages.
EP Application No. 18777889.9, Office Action mailed Nov. 5, 2025; Applicant Chase Therapeutics Corporation; 6 pages.
EP Application No. 24189957.4, Office Action dated Jun. 3, 2026; Applicant Alto Neuroscience, Inc.; 7 total pages.
EP Application No. EP26159147.3, Extended European Search Report mailed May 22, 2026; Applicant Alto Neuroscience.; 13 pages.
Minami, M., et al., "Pharmacological aspects of anticancer drug-induced emesis with emphasis on serotonin release and vagal nerve activity," Pharmacology & Therapeutics (2003), vol. 99, pp. 149-165; doi: 10.1016/S0163-7258(03)00057-3.
PCT Application No. PCT/US2024/062080, International Preliminary Report on Patentability mailed Jul. 9, 2026, Applicant ALTO Neuroscience, Inc.; 22 pages.
PCT Application No. PCT/US2026/030325, International Search Report and Written Opinion mailed Aug. 13, 2026, Applicant Alto Neuroscience, Inc.; 11 pages.
PCT Application No. PCT/US2026/030400, Invitation to Pay Additional Fees and, Where Applicable, Protest Fee, mailed Aug. 7, 2026, Applicant Alto Neuroscience, Inc.; 3 pages.
Szegedi et al., "Pramipexole in major depression—An open clinical trial," European Neuropsychopharmacology, Jun. 1996, vol. 6, p. 142.
U.S. Appl. No. 19/653,745, Non-Final Office Action mailed Jul. 29, 2026; Inventor Clarence-Smith, Kathleen E et al.; 11 pages.

* cited by examiner

COMBINATION THERAPY FOR A DOPAMINE AGONIST

CROSS-REFERENCE TO RELATED APPLICATIONS

This application is a continuation of U.S. application Ser. No. 19/390,174, filed Nov. 14, 2025, which is a continuation of U.S. application Ser. No. 19/244,143, filed Jun. 20, 2025, now U.S. Pat. No. 12,521,374, which is a continuation of U.S. application Ser. No. 16/607,252, filed Oct. 22, 2019, which is a U.S. National Phase Application of PCT/US2018/028885, filed Apr. 23, 2018, which claims priority from U.S. Provisional Application No. 62/489,016, filed Apr. 24, 2017, the disclosures of which are incorporated by reference herein in their entireties for all purposes.

FIELD OF THE INVENTION

The present invention pertains to the field of the treatment of depression.

Object of the Invention

The present invention concerns pharmaceutical combinations, including fixed-dose combinations, comprising a 5HT3-antagonist and an effective pramipexole dose, for the treatment of major depressive disorders.

DEFINITIONS

"CGI": Clinical Global Impression.

"CNS": Central Nervous System.

"IR": Immediate Release of the active ingredient from a composition.

"ER": Extended Release of the active ingredient from a composition.

"GI": Gastro-Intestinal.

"AE(s)": Adverse Effect(s).

"DSM-5": Diagnostic and Statistical Manual of Mental Disorders, 5th edition.

"HAMD": Hamilton Depression Rating Scale.

"MADRS": Montgomery and Asberg Depression Rating Scale.

"MDD": Major Depressive Disorder.

"MAOIs": Monoamine oxidase inhibitors.

"NIMH": National Institute of Mental Health.

"PD": Parkinson's Disease.

"Persistent depressive disorder": also called dysthymia.

"PMDD": Premenstrual Dysphoric Disorder.

"5HT3-antagonist": an antagonist of the serotonin receptor subtype-3, in the literature also referred to as a 5-HT3 receptor antagonist or a 5-HT3 receptor inhibitor.

"Effective daily dose of 5HT3-antagonist": as used herein, refers to a daily dose of said 5HT3-antagonist of from 1 μg to 300 mg.

"Effective dose/unit form of a 5HT3-antagonist" or "effective dose per unit form of a 5HT3-antagonist": an amount of said 5HT3-antagonist per unit form in the range of from 1 μg to 300 mg.

"Pramipexole": the(S)-6-propylamino-4,5,6,7-tetrahydro-1,3-benzothiazole-2-amine, as active principle including the free base and its pharmaceutically acceptable salts and solvates, unless otherwise specified.

"Effective daily dose of pramipexole" or "therapeutically effective dose of pramipexole": a daily pramipexole dose equivalent to at least a pramipexole dihydrochloride monohydrate approved daily dose for the symptomatic treatment of PD, this effective daily dose including low daily doses used during the titration period.

"Effective dose/unit form" or "effective dose per unit form", in reference to pramipexole: a pramipexole amount per unit form equivalent to at least a pramipexole dihydrochloride monohydrate amount per unit form approved for the symptomatic treatment of PD, this amount including low amounts per unit form used during the titration period.

"Salts or solvates thereof" or "salts and solvates thereof", with reference to any 5HT3-antagonist or to pramipexole: this expression indicates that any salt of said pramipexole or said 5HT3-antagonist may be solvated with a solvent, normally water.

"SSRIs": Selective serotonin reuptake inhibitors.

"NDRIs": Norepinephrine-dopamine reuptake inhibitors.

"TCAs": Tricyclic antidepressants.

"TTS": Transdermal Therapeutic System.

"Depressive disorders": include, but is not limited to, major depressive disorder (MDD), persistent depressive disorder (dysthymia), Bipolar depression, seasonal affective disorder (SAD), psychotic depression, premenstrual dysphoric disorder (PDD), peripartum (postpartum) depression, situational depression, and atypical depression. The common feature of these depressive disorders is the presence of sad, empty, or irritable mood, accompanied by somatic and cognitive changes that significantly affect the individual's capacity to function. The difference among these disorders are issues of duration, timing or presumed etiology. See Depressive Disorders, Diagnostic and Statistical Manual of Mental Disorders, Fifth Edition, dsm.psychiatryonline.org/doi/10.1176/appi.books.9780890425596.dsm04.

BACKGROUND OF THE INVENTION

Major depressive disorder (MDD), also referred to as depression or clinical depression, is a common but serious mood disorder associated with a significant burden, affecting around 16% of the population in the US in their lifetime (reviewed in de Sousa et al, 2015). Depression is one of the most common mental disorders in the U.S. Current research suggests that depression is caused by a combination of genetic, biological, environmental, and psychological factors.

The estimated costs of MDD are around 83 billion US Dollars annually, due to many psychosocial factors including loss of workdays (reviewed in de Sousa et al, 2015). Estimates are that on average a depressed person loses 27.2 workdays per year (reviewed in de Sousa et al, 2015). A significant part of the burden corresponds to unsuccessful treatments. Remission of depressive symptoms is achieved in only one-third of the MDD patients after the first antidepressant trial (reviewed in de Sousa et al, 2015), and unsuccessful treatments contribute substantially to the observed suffering and social costs of MDD.

Signs and symptoms of depression typically consist of the following: persistent sad, anxious, or "empty" mood; feelings of hopelessness or pessimism; irritability; feelings of guilt, worthlessness, or helplessness; loss of interest or pleasure in hobbies and activities; decreased energy or fatigue; moving or talking more slowly; feeling restless or having trouble sitting still; difficulty concentrating, remembering, or making decisions; difficulty sleeping, early-morning awakening, or oversleeping; appetite and/or weight changes; thoughts of death or suicide, or suicide attempts; aches or pains, headaches, cramps, or digestive problems without a clear physical cause and/or that do not ease even with treatment (NIMH, Health and Education, Mental Health Information as posted on the NIMH Web Site). Not everyone who is depressed experiences every symptom. Some people experience only a few symptoms while others may experience many. For a diagnosis of depression, signs and symptoms have to be present most of the day, nearly every day, for at least two weeks (DSM-5).

Depression can happen at any age (NIMH, Health and Education, Mental Health Information as posted on the NIMH Web Sit), but often begins in adulthood. Depression is now recognized as occurring in children and adolescents, although it sometimes presents with more prominent irritability than low mood. Depression, especially in midlife or older adults, can co-occur with other serious medical illnesses, such as diabetes, cancer, heart disease, and Parkinson's disease. Risk factors include: personal or family history of depression; major life changes, trauma, or stress; certain physical illnesses and medications.

Some forms of depression are slightly different, or develop under unique circumstances (NIMH, Health and Education, Mental Health Information as posted on the NIMH Web Sit), such as:

- Persistent depressive disorder (also called dysthymia), with early or late onset and with or without atypical features, is a depressed mood that lasts for at least two years. A person diagnosed with persistent depressive disorder may have episodes of major depression along with periods of less severe symptoms, but symptoms must last for two years to be considered persistent depressive disorder.
- Perinatal depression is much more serious than the "baby blues" (relatively mild depressive and anxiety symptoms that typically clear within two weeks after delivery) that many women experience after giving birth. Women with perinatal depression experience full-blown major depression during pregnancy or after delivery (postpartum depression). The feelings of extreme sadness, anxiety, and exhaustion that accompany perinatal depression may make it difficult for these new mothers to complete daily care activities for themselves and/or for their babies.
- Psychotic depression occurs when a person has severe depression plus some form of psychosis, such as having disturbing false fixed beliefs (delusions) or hearing or seeing upsetting things that others cannot hear or see (hallucinations). The psychotic symptoms typically have a depressive "theme," such as delusions of guilt, poverty, or illness.
- Seasonal affective disorder is characterized by the onset of depression during the winter months, when there is less natural sunlight. This depression generally lifts during spring and summer. Winter depression, typically accompanied by social withdrawal, increased sleep, and weight gain, predictably returns every year in seasonal affective disorder.
- Mood dysregulation disorder (diagnosed in children and adolescents; DSM-5).
- Premenstrual Dysphoric Disorder (PMDD; DSM-5).
- Bipolar Disorder is different from depression, but it is included in this list since patients with bipolar disorder experience episodes of extremely low moods that meet the criteria for major depression (called "bipolar depression"). Bipolar disorder is a persistent, episodic and debilitating condition with an estimated lifetime prevalence of over 2.0%, including both types I (with mania) and II (with hypomania) (reviewed in Poon et al, 2015). Bipolar disorder is associated with recurring episodes of mania, hypomania, mixed manic depressive states, or psychosis, as well as prominent major depression and dysthymia, as well as prevalent anxiety symptoms all leading to high risks of potentially severe functional impairment, substance abuse, and high rates of suicide, accidents, and increased mortality from co-occurring medical illnesses-all despite use of available pharmacological and psychosocial treatments (Poon et al, 2015). The depressive components of the disorder have been especially difficult to treat successfully and they account for three-quarters of the nearly 50% of weeks of follow-up with treatment that include clinically significant residual morbidity (reviewed in Poon et al, 2015).

Other mood disorders encompassed within the term "depression" include Alzheimer's disease with depressed mood, depressed mood in Parkinson's disease, Lewy body disease, and other dementias, post-stroke depression, schizoaffective disorders, adjustment disorder with depressed mood, and drug- and alcohol-induced depressed mood.

Depression is usually initially treated with medications and psychotherapy. If the treatments do not reduce symptoms, electroconvulsive therapy and other brain stimulation therapies may help. Medications include the following (Mayo Clinic):

- Selective serotonin reuptake inhibitors (SSRIs) such as fluoxetine (Prozac), paroxetine (Paxil, Pexeva), sertraline (Zoloft), citalopram (Celexa) and escitalopram (Lexapro).
- Serotonin-norepinephrine reuptake inhibitors (SNRIs) such as duloxetine (Cymbalta), venlafaxine (Effexor XR), desvenlafaxine (Pristiq, Khedezla) and levomilnacipran (Fetzima).
- Norepinephrine-dopamine reuptake inhibitors (NDRIs) such as bupropion (Wellbutrin, Aplenzin, Forfivo XL).
- Atypical antidepressants such as trazodone and mirtazapine (Remeron), vortioxetine (Brintellix), and vilazodone (Viibryd).
- Tricyclic antidepressants (TCAs) such as imipramine (Tofranil), nortriptyline (Pamelor), amitriptyline, doxepin, trimipramine (Surmontil), desipramine (Norpramin) and protriptyline (Vivactil). These can be very effective, but tend to cause more-severe side effects than newer antidepressants. Tricyclics are therefore usually considered as second line therapy.
- Monoamine oxidase inhibitors (MAOIs), such as tranylcypromine (Parnate), phenelzine (Nardil) and isocarboxazid (Marplan), may be prescribed, typically when other medications haven't worked. However, MAOIs are usually not first line antidepressant therapy, because they can have serious interactions with certain foods and some medications including birth control pills, decongestants and certain herbal supplements. Selegiline TTS (Emsam), a newer MAOI, may cause fewer side effects than other MAOIs.

One disadvantage of all of the above antidepressant medications is that they typically take 2 to 4 weeks to start having an antidepressant effects.

(S)-6-propylamino-4,5,6,7-tetrahydro-1,3-benzothiazole-2-amine (pramipexole) is a synthetic aminothiazole derivative, described in U.S. Pat. No. 4,886,812, the content of which is incorporated herein by reference. It is a dopamine autoreceptor agonist (Schneider and Mierau 1987) that is approved for the "treatment of signs and symptoms of early Parkinson's disease" (herein below referred to as "symptomatic treatment of PD"), in doses ranging from 0.375 mg/day to 4.5 mg/day, given in 3 equally divided doses (Mirapex® Prescribing Information, July 2016). Pramipexole is supplied in tablets for immediate release containing 0.125 mg, 0.25 mg, 0.5 mg, 1 mg and 1.5 mg of pramipexole dihydrochloride monohydrate; and in tablets for extended release containing 0.375 mg, 0.75 mg, 1.5 mg, 3 mg and 4.5 mg of pramipexole dihydrochloride monohydrate. It is structurally distinct from the ergot-derived drugs (ergoline class, e.g., bromocriptine and pergolide). Pramipexole is a dopamine D2 receptor agonist that is also pharmacologically unique in that it is a full agonist and has receptor selectivity for the dopamine D3 receptor subtype of the D2 subfamily of receptors. These properties may confer advantages in terms of both efficacy (full agonist with potential for greater therapeutic effects) and safety (receptor selectivity may reduce unwanted side effects) compared to currently available dopamine agonists [Piercey, 1998].

Pramipexole was also found to be effective in the treatment of depressive symptoms in patients with PD, albeit with a small effect size. A 12-week, double-blind, placebo controlled trial in 296 PD patients was conducted with pramipexole (0.125 to 1.0 mg/kg). The primary endpoint was the Beck Depression Inventory scale (BDI). Results showed that BDI scores decreased by an adjusted 5.9 (SE 0.5) in the pramipexole group, and 4.0 (SE 0.5) in the placebo group. The difference between the 2 treatment groups was significant (p=0.01; Barone et al., 2010), although the magnitude of the effect size was small. In addition, other small, often open-label studies in which pramipexole was added on to antidepressant treatment (augmentation) also showed modest but significant efficacy in favor of pramipexole in non-PD patients with major depressive disorder (MDD; Cusin et al., 2013; Goldberg et al, 2004), including non-PD patients with treatment resistant depression (Hori and Kunigi, 2012; Pae, et al., 2013; Fawcett et al., 2016), and patients with depression associated with bipolar disorder (reviewed in Sienaert et al., 2013; Dell'Osso and Ketter, 2013; Tondo et al., 2014; et al, 2016). However, Kleebatt et al. (2017) in their review judged that clear proof of antidepressant efficacy had not been obtained for pramipexole, and attributed this to low levels of evidence, small sample sizes or discordant results. In all these reports, the dose of pramipexole remained within the range approved for the treatment of PD, even when the title of the publication mentions "high doses" of pramipexole (Fawcett et al., 2016). Since in most of these studies, efficacy appeared to be modest, higher doses of pramipexole were tested in a randomized, prospective, double-blind, placebo-controlled, fixed-dose study (Corrigan et al., 2000). A total of 174 eligible patients with a DSM-III-R diagnosis of major depression (single or recurrent episode, with or without melancholia and without psychotic features) were assigned to one of five treatment groups: placebo group, fluoxetine group (20 mg/day), or one of three pramipexole groups (0.375 mg/day; 1 mg/day; 5 mg/day). Patients received a 1-week placebo run-in, 8 weeks of treatment, and a 1-week post-study follow-up assessment (week 9). Efficacy was measured primarily by the change from baseline in the HAM-D (17-item version) total score, MADRS total score, and the CGI-Severity of Illness (SI) score. Results showed that the majority of patients in each treatment group completed the study (66-86%), with the exception of the pramipexole 5.0 mg group (45.4%). In the pramipexole 5.0 mg group, 57.6% of patients discontinued treatment prematurely, mainly because of adverse events (AEs), 76% of patients reported nausea, and 39% reported vomiting. At endpoint (week 8), the pramipexole 1.0 mg group and the fluoxetine group showed significantly better improvement over baseline than the placebo group on the HAMD (p=0.0076) and on the MADRS. The pramipexole 5.0 mg group had the best improvement at week 8 (−15.00), but p values were not available for this test against placebo because of the high drop-out rate.

Taken together, the results reported by Corrigan et al. (2000) suggest that higher doses of pramipexole could be more effective, but doses higher than the approved doses cannot be used because of a high incidence of dose-limiting adverse events (AEs), notably nausea and vomiting. Also, previously, animal studies suggested that high doses of pramipexole should be more effective for the treatment of depression. For example, high doses of pramipexole proved to be active in diverse tests of animal behavior simulating symptoms of depression, including Willner's Anhedonia Test (Willner et al., 1994), Fixed Interval Test, Forced Swimming Test, and REM Sleep Inhibition Test.

The present inventors, in a different therapeutic context, disclosed the ability to increase the doses of an acetylcholinesterase inhibitor by combining said acetylcholinesterase inhibitor with an antiemetic agent, including 5HT3-antagonists, in US 2011/0071135.

The document US 2014/0024644 (see also WO 2014/014951 and WO 2014/014962) discloses indole and indazole-acetic acid or -acetamide derivatives, esterified or N-substituted with azabicycloalkyl or oxaazabicycloalkyl groups, endowed with a 5HT3-antagonist activity. The compounds described therein are asserted to be useful for the treatment of diseases treatable by inhibition of the 5HT3 receptor. This document enumerates a series of disorders that may be treated with a 5HT3-antagonist: emesis, migraine, substance abuse and addiction, neurodegenerative and psychiatric disorders (including depression), gastrointestinal disorders, immunological disorders, atherosclerosis and inflammation. The document also discloses the possible combination of said 5HT3-antagonists with six classes of neuroleptic agents and with a great number of active agents including pramipexole. This document neither mentions nor suggests any possible combination with pramipexole for the treatment of a MDD.

In conclusion, notwithstanding the massive literature reporting the possibility of an enhanced pramipexole antidepressant efficacy linked to an increase of the pramipexole dose, in particular the Willner et al 1994, Corrigan et al 2000, and US 2011/0071135 disclosures, pramipexole remains practically inactive in the treatment of depression.

Thus, the problem of providing safe, chronic, effective treatment of a patient suffering from depression with pramipexole is not yet solved.

SUMMARY OF THE INVENTION

The present invention relates to increasing the therapeutic window for pramipexole, for the treatment of depressive disorders such as MDD, to safely enable its full antidepressant efficacy. In particular, the present invention relates to a combination of pramipexole with a 5HT3-antagonist to increase the therapeutic window for pramipexole.

It has been found that ondansetron or a pharmaceutically acceptable salt or solvate thereof, by reducing or even abrogating the GI side effects of high doses of pramipexole enables the full antidepressant potential of pramipexole.

It has also been found that, by using said 5HT3-antagonist, in combination with pramipexole or a pharmaceutically acceptable salt or solvate thereof, it is possible to safely treat a patient suffering from depression by maintaining a therapeutically effective pramipexole daily dose with minimal adverse effect.

The combination of said 5HT3-antagonist with pramipexole or a pharmaceutically acceptable salt or solvate thereof enables the full antidepressant efficacy of pramipexole.

For example in the case of pramipexole dihydrochloride monohydrate, its combination with said 5HT3-antagonist allows the administration of a therapeutically effective dose of said pramipexole dihydrochloride monohydrate that, in many patients, significantly exceeds the aforementioned maximum recommended dose (4.5 mg/day) of pramipexole dihydrochloride monohydrate for the treatment of the symptoms of PD, thus increasing its efficacy in the treatment of a patient suffering from a MDD.

More particularly, it has been found that, in patients suffering from a depressive disorder, doses of pramipexole equivalent to a range of from 5 mg to 45 mg per dose, or from 5 mg to 45 mg/day, normally from 5 mg to 20 mg/day, of pramipexole dihydrochloride monohydrate, in combination with a 5HT3-antagonist, offer significant efficacy and a fast onset of action. Advantageously, in combination with a 5HT3-antagonist, pramipexole daily doses equivalent to from more than 4.5 mg to 45 mg, from 5 mg to 45 mg, from more than 6 mg to 45 mg or from 6.5 mg to 45 mg, normally from more than 6 mg to 20 mg or from 6.5 to 20 mg of pramipexole dihydrochloride monohydrate provide safe treatment for patients suffering from MDD.

Hitherto, notwithstanding the aforementioned massive literature reporting the possibility of pramipexole antidepressant efficacy, no one suspected that major depressive disorders could be safely cured by using a pramipexole/5HT3-antagonist combination at the currently used pramipexole daily doses and also at daily doses higher, and even much higher than those recommended for the treatment of PD, and substantially without the inherent pramipexole adverse effects.

Thus, the present invention provides a pharmaceutical combination comprising (a) a 5HT3-antagonist; and (b) pramipexole or a pharmaceutically acceptable salt or solvate thereof, in an effective daily dose, for use for the treatment of depressive disorders such as MDD. [

According to a first aspect, the present invention provides the use of (or a method using) a 5HT3-antagonist for enabling the full antidepressant efficacy of pramipexole in the treatment of MDD.

More precisely, according to this first aspect, the invention provides a 5HT3-antagonist, for use in the treatment of a MDD, in combination with an effective daily dose of pramipexole. Said effective pramipexole daily dose may be higher, and even much higher than the maximum daily dose recommended in the treatment of PD.

According to this first aspect, the invention also provides a method for treating a patient suffering from a major depressive disorder, which comprises treating said patient with a 5HT3-antagonist, in combination with an effective daily dose of pramipexole or a pharmaceutically acceptable salt or solvate thereof. Said effective daily dose (in pramipexole dihydrochloride monohydrate) can significantly and safely exceed the maximum dose of pramipexole dihydrochloride monohydrate recommended for the symptomatic treatment of PD.

Thus, according to this first aspect, the method (or use) provides the safe administration of a 5HT3-antagonist in combination with pramipexole daily doses (in pramipexole dihydrochloride monohydrate) of from 0.375 mg to 45 mg. For each patient, after the initial titration starting at a daily dose of 0.375 mg, said daily dose is gradually increased to a dose regiment of from 3 mg to 45 mg, preferably from more than 4.5 mg to 45 mg, from 5 mg to 45 mg, from more than 6 mg to 45 mg or from 6.5 mg to 45 mg, normally from more than 4.5 mg to 20 mg, from 5 mg to 20 mg, from more than 6 mg to 20 mg, or from 6.5 mg to 20 mg.

In particular, the invention provides a method (or the use of said 5HT3-antagonist) for treating a patient suffering from a major depressive disorder, which comprises treating said patient with said 5HT3-antagonist, in combination with a pramipexole or a pharmaceutically acceptable salt or solvate thereof at a daily dose equivalent to from more than 4.5 mg to 45 mg, preferably from 5 mg to 45 mg, from more than 6 mg to 45 mg or from 6.5 mg to 45 mg of pramipexole dihydrochloride monohydrate.

Normally, as set forth above, said pramipexole daily dose, depending on the degree of gravity of the illness and the age and condition of the patient, will be equivalent to from 5 mg to 20 mg from more than 6 mg to 20 mg, or from 6.5 mg to 20 mg of pramipexole dihydrochloride monohydrate.

According to a second aspect, the invention provides the use of said 5HT3-antagonist for the preparation of a medicament consisting of a pharmaceutical composition comprising, as an active ingredient, said 5HT3-antagonist, in admixture with a pharmaceutical carrier or vehicle, for preventing or curing the AEs of pramipexole or of a pharmaceutically acceptable salt and/or solvate thereof in the treatment of MDD, and also, principally, for administering said pramipexole to a patient suffering from MDD at doses higher, and even much higher than the maximum recommended doses approved for the treatment of PD, thus increasing the pramipexole efficacy in combating MDD.

In particular, according to this second aspect, the invention provides the use of a 5HT3-antagonist for the preparation of a medicament consisting of a pharmaceutical composition comprising, as an active ingredient, said 5HT3-antagonist, in admixture with a pharmaceutical carrier or vehicle, for the treatment of a MDD in combination with an effective daily dose of pramipexole or a pharmaceutically acceptable salt or solvate thereof.

Preferably, according to this second aspect, the invention provides the use of a 5HT3-antagonist for the manufacture of a medicament for the safe treatment of a MDD, in combination with pramipexole or a pharmaceutically acceptable salt or solvate thereof at a daily dose (in pramipexole dihydrochloride monohydrate) that can significantly and safely exceed the maximum dose of pramipexole dihydrochloride monohydrate recommended for the symptomatic treatment of Parkinson's disease. As described above, said daily dose (in pramipexole dihydrochloride monohydrate) is from 0.375 mg to 45 mg, in particular from more than 4.5 mg to 45 mg, from 5 mg to 45 mg, from more than 6 mg to 45 mg or from 6.5 mg to 45 mg, normally from 5 mg to 20 mg, from more than 6 mg to 20 mg or from 6.5 mg to 20 mg.

According to an embodiment, for said method (or use), said 5HT3-antagonist and said pramipexole or pharmaceutically acceptable salt or solvate thereof are each formulated in a pharmaceutical composition in admixture with a pharmaceutical carrier or vehicle and separately administered, concurrently or sequentially, to the patient in need of treatment with said combination, in particular to a patient suffering from a MDD. Normally, said compositions are in dosage unit form.

According to another embodiment, for said use or said method, said 5HT3-antagonist and said pramipexole or pharmaceutically acceptable salt or solvate thereof are mixed together and formulated in a pharmaceutical composition (fixed-dose combination), in admixture with a pharmaceutical carrier or vehicle, to be administered to the patient suffering from a MDD, in need of said treatment. Normally, said compositions are in dosage unit form.

A 5HT3-antagonist indicated for the prevention of post-operative nausea and vomiting or of chemotherapy-induced nausea and vomiting may preferably be used in combination with a dose of pramipexole that is generally currently used for treating PD, or with a higher, and even much higher dose. The use of this combination significantly improves the conditions of patients suffering from a MDD by concurrently mitigating or even eliminating the pramipexole adverse effects, otherwise intolerable when using said pramipexole alone.

According to the present invention, preferably, said 5HT3-antagonists used are those shown to be effective in or approved for the prevention or treatment of postoperative nausea and vomiting or for the prevention of the chemotherapy-induced nausea and vomiting. In fact, surprisingly, 5HT3 receptor inhibitors, known to block nausea, vomiting, and diarrhea induced by chemotherapeutic drugs, have been shown, in particular when administered at high doses, to also block the gastro-intestinal side effects of pramipexole without affecting its efficacy in treating said MDD.

This finding is surprising because, notwithstanding the gravity of the illnesses and the fact that both said 5HT3-antagonists and pramipexole were two families of products in use during more than a decade, each in its own indication, to date no one thought that, by combining an effective dose of said 5HT3-antagonist with an effective dose of pramipexole, it would be possible to safely improve the conditions of patients suffering from a MDD, by also allowing an increase of the pramipexole therapeutic dose, in particular the dose of pramipexole dihydrochloride monohydrate.

According to yet a further embodiment, the invention provides a pharmaceutical fixed-dose combination consisting of a pharmaceutical composition comprising an effective dose/unit form of a 5HT3-antagonist, as Component (a) and an effective dose/unit form of pramipexole, as Component (b), in admixture with a pharmaceutical carrier or vehicle.

In said combination, Component (a) is present in said composition in an amount per unit form of from 1 μg to 300 mg; and Component (b) is present in said composition in an amount per unit form equivalent to from 0.125 mg to 45 mg, normally from 0.125 mg to 20 mg of pramipexole dihydrochloride monohydrate.

The dose per unit form of pramipexole or pharmaceutically acceptable salt or solvate thereof, in pramipexole dihydrochloride monohydrate, will normally be in a range selected from the group consisting of from 1.5 mg to 20 mg, from 1.625 mg to 20 mg, from 3 mg to 20 mg, from 5 mg to 20 mg, from more than 6 mg to 20 mg and from 6.5 mg to 20 mg.

DETAILED DESCRIPTION

The present invention relates to a pharmaceutical combination comprising a 5HT3-antagonist, preferably shown effective or indicated for the prevention of post-operative nausea and vomiting or of the chemotherapy-induced nausea and vomiting, for use for the treatment of MDD in combination with pramipexole; and to the use of a pharmaceutical combination comprising said 5HT3-antagonist and pramipexole, for the preparation of a medicament for treatment of MDD comprising an effective dose per unit form of pramipexole. Said effective dose may be higher, and even much higher than the pramipexole maximum daily dose recommended in the treatment of PD.

More particularly, the invention concerns, according to its aspects,

- a method for the treatment of a MDD in a patient in need of said treatment, which comprises administering to said patient a 5HT3-antagonist in combination with a therapeutically effective pramipexole daily dose;
- a 5HT3-antagonist for use for the treatment of a MDD in a patient in need of said treatment, in combination with a therapeutically effective daily dose of pramipexole; and
- the use of a 5HT3-antagonist for the manufacture of a medicament for the treatment of a MDD in a patient in need of said treatment, in combination with a therapeutically effective daily dose of pramipexole.

The invention also provides the use of said 5HT3-antagonist for the preparation of a medicament for the treatment of MDD in a fixed-dose combination consisting of a pharmaceutical composition comprising said 5HT3-antagonist and said pramipexole.

The 5HT3-Antagonist

Any of the 5HT3-antagonists, especially those shown effective or indicated for the prevention of post-operative nausea and vomiting or of the chemotherapy-induced nausea and vomiting may be used in combination with a dose of pramipexole that is generally currently used for treating PD, or with a higher and even much higher dose.

The chronic use of this combination improves the condition of a patient suffering from a MDD, by concurrently mitigating or even eliminating the adverse effects induced by said pramipexole.

According to the present invention, preferably, said 5HT3-antagonists used are those approved for preventing nausea and vomiting following cancer chemotherapy.

A useful 5HT3-antagonist is selected from the group consisting of 5-methyl-2-[(4-methyl-1H-imidazol-5-yl)methyl]-2,3,4,5-tetrahydro-1H-pyrido[4,3-b]indol-1-one (alosetron) and pharmaceutically acceptable salts and solvates thereof, especially its hydrochloride, disclosed in U.S. Pat. No. 5,360,800; (+)-6-chloro,3,4-dihydro-4-methyl-3-oxo-N-(quinuclidinyl)-2H-1,4-benzoxazine-8-carboxamide (azasetron) and pharmaceutically acceptable salts and solvates thereof, especially its hydrochloride, disclosed in U.S. Pat. No. 4,892,872; [(1S,5R)-8-methyl-8-azabicyclo[3.2.1]octan-3-yl] 3,5-dichlorobenzoate (bemesetron, CAS: 40796-97-2); (10R)-10-[(2-methyl-1H-imidazol-1-yl)methyl]-5,6,9,10-tetrahydro-4H-pyrido (3,2,1-jk) carbazol-11-one (cilansetron) and pharmaceutically acceptable salts and solvates thereof, especially its hydrochloride monohydrate, disclosed in U.S. Pat. No. 4,939,136; (3R)-10-oxo-8-azatricyclo[5.3.1.0$^{3,8}$]undec-5-yl 1H-indole-3-carboxylate (dolasetron) and pharmaceutically acceptable salts and solvates thereof, especially it monomethanesulfonate monohydrate, disclosed in U.S. Pat. No. 4,906,755; (+)-(R)-8,9-dihydro-10-methyl-7-[(5-methylimidazol-4-yl)methyl]pyrido[1,2-a]indol-6 (7H)-one (fabesetron) and pharmaceutically acceptable salts and solvates thereof, especially its hydrochloride or maleate, disclosed in U.S. Pat. No. 5,141,945; 1-methyl-N-((1R,3r,5S)-9-methyl-9-azabicyclo[3.3.1]nonan-3-yl)-1H-indazole-3-carboxamide (granisetron) and pharmaceutically acceptable salts and solvates thereof, especially its hydrochloride, disclosed in U.S. Pat. No. 4,886,808; 2,3-dihydro-N-(8-methyl-8-azabicyclo[3.2.1]oct-3-yl)-2-oxo-1H-benzimidazole-1-carboxamide (itasetron) and pharmaceutically acceptable salts and solvates thereof, especially its hydrochloride, disclosed in U.S. Pat. No. 5,223,511; 1-phenylmethyl-2-(1-piperazinyl)-1H-benzimidazole (lerisetron) and pharmaceutically acceptable salts and solvates thereof, specially its hydrochloride, disclosed in U.S. Pat. No. 5,256,665 and, in a transdermal preparation, in U.S. Pat. No. 6,136,807; 6-fluoro-5-methyl-2-[(5-methyl-1H-imidazol-4-yl)methyl]-2,3,4,5-tetrahydro-1H-pyrido[4,3-b]indol-1-one (lurosetron, CAS 128486-54-4) and pharmaceutically acceptable salts and solvates thereof, especially its mesylate (GR 87445 N); (±) 1,2,3,9-tetrahydro-9-methyl-3-[(2-methyl-1H-imidazol-1-yl)methyl]-4H-carbazol-4-one (ondansetron) and pharmaceutically acceptable salts and solvates thereof, especially its hydrochloride dihydrate, disclosed in U.S. Pat. No. 4,695,578; (3aS)-2-[(S)-1-azabicyclo [2.2.2]oct-3-yl]-2,3,3a,4,5,6-hexahydro-1-oxo-1H-benz [de]isoquinoline (palonosetron) and pharmaceutically acceptable salts and solvates thereof, especially its hydrochloride, disclosed in U.S. Pat. No. 5,202,333; 1-methylindol-3-yl)-[(5R)-4,5,6,7-tetrahydro-3H-benzimidazol-5-yl] methanone (ramosetron) and pharmaceutically acceptable salts and solvates thereof, especially its fumarate, disclosed in U.S. Pat. No. 5,344,927; endo-N-(8-methyl-8-azabicyclo [3.2.1]oct-3-yl)-2,3-dihydro-3,3-dimethyl-(3,3-dimethyl-N-1αH,5αH-tropan-3α-yl-1-indole-1-carboxamide indolinecarboxamide, ricasetron, CAS 117086-68-7) and pharmaceutically acceptable salts and solvates thereof, especially its hydrochloride; the (3-endo)-8-methyl-8-azabicyclo [3.2.1]oct-3-yl ester of 1H-indole-3-carboxylic acid (3-tropanylindole-3-carboxylate, tropisetron) and pharmaceutically acceptable salts and solvates thereof, especially its hydrochloride, disclosed in U.S. Pat. No. 4,789,673; and 5-chloro-2,2-dimethyl-N-(8-methyl-8-azabicyclo [3.2.1]oct-3-yl)-2,3-dihydro-1-benzofuran-7-carboxamide (zatosetron) and pharmaceutically acceptable salts and solvates thereof, especially its maleate, disclosed in U.S. Pat. No. 5,563,148; the disclosures of all the US patents cited in this paragraph being incorporated herein in their entirety by reference.

Advantageously, said 5HT3-antagonist is selected from the group consisting of azasetron and pharmaceutically salts and solvates thereof, dolasetron and pharmaceutically acceptable salts and solvates thereof, granisetron and pharmaceutically salts and solvates thereof, ondansetron and pharmaceutically salts and solvates thereof, palonosetron and pharmaceutically salts and solvates thereof, ramosetron, and pharmaceutically salts and solvates thereof and tropisetron and pharmaceutically salts and solvates thereof.

Illustrative examples of salts of said 5HT3-antagonists and of said pramipexole include acid addition salts with mineral acids such as hydrochloric acid, hydrobromic acid, hydriodic acid, sulfuric acid, nitric acid, phosphoric acid and the like or with organic acids such as formic acid, acetic acid, propionic acid, oxalic acid, malonic acid, succinic acid, fumaric acid, maleic acid, lactic acid, malic acid, tartaric acid, citric acid, carbonic acid, methanesulfonic acid, ethanesulfonic acid, aspartic acid, glutamic acid and the like. The solvation agent is generally water.

Antagonists of the 5HT3 receptor available for the prevention or treatment of postoperative nausea and vomiting or for the prevention of chemotherapy-induced nausea and vomiting are particularly useful according to the present invention. In particular, azasetron hydrochloride, commercially available in 10 mg tablet, and in 10 mg vials for intravenous injection; dolasetron monomethanesulfonate monohydrate (also referred to as dolasetron mesylate), commercially available in 200 mg maximal dose tablet, and in 12.5 mg/0.625 ml vial; granisetron hydrochloride, commercially available in 2.24 mg maximal dose tablet; ondansetron hydrochloride dihydrate, commercially available in 10 mg maximal dose tablet and in a 2 mg/ml (in ondansetron base) solution available as a 20 ml multidose vial; palonosetron hydrochloride, commercially available in 0.28 mg/5 mL injection and 0.56 mg capsule and in 0.075 mg/1.5 ml or 0.25 mg/5 ml (in palonosetron base) vials; ramosetron, commercially available in 0.15 mg/ml injection and in 0.1 mg oral tablet; and tropisetron hydrochloride, commercially available in 5.64 mg capsules, in 2.256 mg/2 ml vials for intravenous injection, and in 5.64-mg vials for intravenous or subcutaneous injection; are particularly advantageous 5HT3-antagonists.

According to the present invention, the 5HT3-antagonist is used in a pharmaceutical composition comprising, as an active ingredient, said 5HT3-antagonist in an amount per unit form of from 1 μg to 300 mg, in admixture with a pharmaceutical carrier or vehicle, and is administered, in combination with a pramipexole daily dose equivalent to from 0.375 mg to 45 mg, normally from more than 4.5 mg to 45 mg, from 5 mg to 45 mg, from more than 6 mg to 45 mg or from 6.5 mg to 45 mg of pramipexole dihydrochloride monohydrate, to a patient suffering from a MDD.

Thus, for example, an oral pharmaceutical composition according to the present invention to be chronically administered in combination with pramipexole may comprise a 5HT3-antagonist selected from the group consisting of azasetron and pharmaceutically acceptable salts and solvates thereof, in an amount per unit form equivalent to from 5 mg to 10 mg of azasetron hydrochloride, to be administered at a daily dose equivalent to from 15 mg to 40 mg of azasetron hydrochloride; dolasetron and pharmaceutically acceptable salts and solvates thereof, in an amount per unit form equivalent to from 25 mg to 200 mg of dolasetron mesylate, to be administered at a daily dose equivalent to from 75 mg to 200 mg of dolasetron mesylate; granisetron and pharmaceutically acceptable salts and solvates thereof, in an amount per unit form equivalent to from 0.5 mg to 2 mg granisetron base, to be administered at a daily dose equivalent to from 1.5 mg to 8 mg of granisetron base; ondansetron and pharmaceutically acceptable salts and solvates thereof, in an amount per unit form equivalent to from 0.5 mg to 16 mg, normally from 2 mg to 8 mg of ondansetron base, to be administered at a daily dose equivalent to from 6 mg to 64 mg, normally from 6 mg to 32 mg of ondansetron base; palonosetron and pharmaceutically acceptable salts and solvates thereof, in an amount per unit form equivalent to from 0.25 mg to 0.5 mg of palonosetron base, to be administered at a daily dose equivalent to from 0.75 mg to 2 mg of palonosetron base; ramosetron and pharmaceutically acceptable salts and solvates thereof, in an amount per unit form equivalent to from 0.05 mg to 0.2 mg of ramosetron hydrochloride, to be administered at a daily dose equivalent to from 0.05 mg to 0.2 mg of ramosetron hydrochloride; and tropisetron and pharmaceutically acceptable salts and solvates thereof, in an amount per unit form equivalent to from 2.5 mg to 5 mg of tropisetron base, to be administered at a daily dose equivalent to from 7.5 mg to 20 mg of tropisetron base.

Preferably, said 5HT3-antagonist is selected from the group consisting of azasetron hydrochloride, in an amount per unit form equivalent to from 5 mg to 10 mg to be administered at a daily dose equivalent to from 15 mg to 40 mg of azasetron hydrochloride; dolasetron mesylate, in an amount per unit form equivalent to from 25 mg to 200 mg of dolasetron mesylate, to be administered at a daily dose equivalent to from 75 mg to 200 mg; granisetron hydrochloride, in an amount per unit form equivalent to from 0.5 mg to 2 mg granisetron base, to be administered at a daily dose equivalent to from 1.5 mg to 16 mg, normally of from 2 mg to 8 mg; ondansetron hydrochloride dihydrate, in an amount equivalent to from 0.5 mg to 32 mg, normally from 2 mg to 32 mg, from 2 mg to 16 mg or from 2 mg to 8 mg ondansetron base, to be administered at a daily dose equivalent to from 6 mg to 64 mg, normally from 6 to 32 mg of ondansetron base; palonosetron hydrochloride, in an amount equivalent to from 0.25 mg to 0.5 mg palonosetron base, to be administered at a daily dose equivalent to from 0.75 to 2 mg of palonosetron base; ramosetron hydrochloride, in an amount per unit form of from 0.05 mg to 02 mg, to be administered at a daily dose of from 0.05 mg to 0.2 mg; and tropisetron hydrochloride, in an amount equivalent to from 2.5 mg to 5 mg tropisetron base, to be administered at a daily dose equivalent to from 7.5 to 20 mg of tropisetron base.

This composition is destined to be administered to a patient suffering from a MDD, in combination with a pharmaceutical composition in dosage unit form comprising pramipexole or a pharmaceutically acceptable salt or solvate thereof, in an amount per unit form in a range equivalent to from 0.125 to 45 mg, preferably from more than 4.5 mg to 45 mg, from more than 6 mg to 45 mg or from 6.5 mg to 45 mg, normally from 3 mg to 20 mg, preferably from more than 5 mg to 20 mg, from more than 6 mg to 20 mg or from 6.5 mg to 20 mg of pramipexole dihydrochloride monohydrate.

The pharmaceutical composition in dosage unit form comprising said 5HT3-antagonist as described above may contain another active ingredient, in particular pramipexole, co-formulated with said 5HT3-antagonist, in admixture with a pharmaceutical carrier or vehicle in a fixed-dose combination.

The Pramipexole

In the combination of the present invention, the beneficial action of the 5HT3-antagonist, counteracting the adverse effects of pramipexole in patients suffering from a MDD, allows for the safe administration of pramipexole daily doses otherwise not tolerable in most of said patients even within the currently approved dose-range (from 0.375 mg to 4.5 mg per day) of pramipexole dihydrochloride monohydrate.

In addition, a 5HT3-antagonist, especially selected among those shown effective or approved for the prevention or treatment of postoperative nausea and vomiting or for the prevention of the chemotherapy-induced nausea and vomiting, renders it possible to safely treat said patients with daily doses of pramipexole or pharmaceutically acceptable salt thereof equivalent to from more than 4.5 mg to 45 mg, from more than 6 mg to 45 mg or from 6.5 mg to 45 mg of pramipexole dihydrochloride dihydrate.

Pharmaceutically acceptable salts of pramipexole are those with inorganic or organic acids such as, but not limited to, hydrochloric acid, hydrobromic acid, sulfuric acid, sulfamic acid, phosphoric acid, nitric acid, acetic acid, propionic acid, stearic acid, glycolic acid, oxalic acid, succinic acid, lactic acid, maleic acid, hydroxymaleic acid, fumaric acid, malic acid, tartaric acid, citric acid, ascorbic acid, phenylacetic acid, glutamic acid, benzoic acid, salicylic acid, 2-acetoxybenzoic acid, methanesulfonic acid, ethanesulfonic acid, 2-hydroxyethanesulfonic (isethionic) acid, p-toluenesulfonic acid, 2-naphthalenesulfonic acid, 4-amino-benzenesulfonic (sulfanilic) acid, 2,6-naphthalenedisulfonic acid, 1,5-naphthalenedisulfonic acid, and pamoic (embonic) acid. The solvation solvent is normally water.

For its administration in combination with the 5HT3-antagonist, pramipexole or a pharmaceutically acceptable salt thereof is formulated in a pharmaceutical composition in dosage unit form comprising an effective dose per unit form of said pramipexole or pharmaceutically acceptable salt thereof, as an active ingredient, in admixture with a pharmaceutical carrier or vehicle. Said active ingredient is formulated according to known technologies for any administration route.

In the case of pramipexole dihydrochloride monohydrate, commercially available, stable pharmaceutical compositions comprising pramipexole dihydrochloride monohydrate, disclosed in WO 2012/0140604 and in WO 2008/122638; and sustained release compositions comprising pramipexole dihydrochloride monohydrate, disclosed in U.S. Pat. No. 8,399,016; may be useful for the use in combination with a 5HT3-antagonist for the treatment of a MDD. The contents of these documents are incorporated herein in their entirety by reference.

In pharmaceutical compositions with a 5HT3-antagonist, the dose per unit form of pramipexole or pharmaceutically acceptable salt or solvate thereof is equivalent to a range selected from the group consisting of from 0.125 mg to 45 mg, from 3 mg to 45 mg, from more than 4.5 mg to 45 mg, from 5 mg to 45 mg, from more than 6 mg to 45 mg and from 6.5 mg to 45 mg of pramipexole dihydrochloride monohydrate. Normally, said dose per unit form is equivalent to a range selected from the group consisting of from 0.125 mg to 20 mg, from 1.6 mg to 20 mg, from 3 mg to 20 mg, from more than 4.5 mg to 20 mg, from 5 mg to 20 mg, from more than 6 mg to 20 mg and from 6.5 mg to 20 mg of pramipexole dihydrochloride monohydrate.

The dose of pramipexole or pharmaceutically acceptable salt or solvate thereof per IR-unit form will preferably be equivalent to a range selected from the group consisting of from 0.125 mg to 22.5 mg, from 3 mg to 22.5 mg, from more than 4.5 mg to 22.5 mg, from more than 6 mg to 22.5 mg and from 6.5 mg to 22.5 mg, normally in a range selected from the group consisting of from 0.125 mg to 10 mg, from 1.5 mg to 10 mg, from 1.625 mg to 10 mg, from 3 mg to 10 mg, from more than 4.5 mg to 10 mg, from 5 mg to 10 mg, from more than 6 mg to 10 mg, and from 6.5 mg to 10 mg of pramipexole dihydrochloride monohydrate, depending on safety and tolerability (in combination with the 5HT3-antagonist).

The dose per unit form of pramipexole or pharmaceutically acceptable salt or solvate thereof in an ER formulation, including slow-release compositions and transdermal therapeutic systems such as transdermal patches, will range from an amount per unit form that is equivalent to a range selected from the group consisting of from 0.375 mg to 45 mg, from 1.5 mg to 45 mg, from 3 mg to 45 mg, from more than 4.5 mg to 45 mg, from 5 mg to 45 mg, from more than 6 mg to 45 mg and from 6.5 mg to 45 mg, of pramipexole dihydrochloride monohydrate, normally equivalent to a range selected from the group consisting of from 0.375 mg to 45 mg, from 1.5 to 20 mg, from 3 mg to 20 mg, from more than 4.5 mg to 20 mg, from 5 mg to 20 mg, from more than 6 mg to 20 mg, and from 6.5 mg to 20 mg of pramipexole dihydrochloride monohydrate, depending on the tolerability (in combination with said 5HT3-antagonist).

As set forth in the Definitions, the above pramipexole doses per unit form include low doses that can be used especially in the case of the initial titration of the pramipexole daily dose or in the less frequent case of the use in the treatment of pediatric depressed patients.

If said 5-HT3 antagonist is ondansetron, the dose per unit form (in ondansetron base) will range from 8 mg to 32 mg.

If said 5-HT3 antagonist is dolasetron, the dose per unit form (in dolasetron mesylate) in combination with pramipexole or pharmaceutically acceptable salt thereof, at the above doses/unit form, will range from 1.5 mg to 200 mg.

First aspect of the invention.

As mentioned above, the present invention provides a pharmaceutical combination comprising (a) said 5HT3-antagonist, and (b) said pramipexole or a pharmaceutically acceptable salt or solvate thereof, at an effective daily dose, for use for the treatment of MDD.

According to a first aspect, the embodiments of the present invention include a 5HT3-antagonist, for use for the treatment of a MDD in a patient in need of said treatment in combination with an effective daily dose of pramipexole or of a pharmaceutically acceptable salt thereof; and a method for treating a patient suffering from a MDD, which comprises administering to a patient in need of said treatment a 5HT3-antagonist in combination with an effective daily dose of pramipexole or a pharmaceutically acceptable salt thereof.

In particular, the present invention provides a method for treating a patient suffering from a major depressive disorder, which comprises treating said patient with an effective dose of a 5HT3-antagonist in combination with an effective daily dose of pramipexole or a pharmaceutically acceptable salt thereof.

Normally, said 5HT3-antagonist is administered at a daily dose of from 1 μg to 300 mg, in combination with a pramipexole effective daily dose, including a daily dose for use during the titration period, equivalent to from 0.375 mg to 45 mg of pramipexole dihydrochloride monohydrate.

As known in the art, in the case of the treatment of patients with drugs potentially inducing severe adverse effects, pramipexole may be used at the lowest doses (daily from 0.375 mg to less than 3 mg or to less than 4.5 mg), in combination with a 5HT3-antagonist, but another advantage provided by the present invention is an increase in the safe titration threshold dose, due to the concomitant presence of said 5HT3-antagonist.

In addition, according to the present invention, the concomitant administration of a 5HT3-antagonist allows for the administration of pramipexole daily doses much higher than the pramipexole dihydrochloride monohydrate maximum daily dose recommended in the treatment of PD.

A 5HT3-antagonist indicated for the prevention of postoperative nausea and vomiting or of chemotherapy-induced nausea and vomiting may be successfully used in combination with pramipexole according to the present invention.

In this case, in carrying out the method (or according to the use) of the present invention, the daily dose of these 5HT3-antagonists is at least as high as that preventing or treating nausea and vomiting in pediatric or adult patients undergoing a surgical operation or cancer chemotherapy according to the current protocols for said treatment or prevention.

Normally, in the method (or use) for the treatment of a MDD according to the present invention, pramipexole or pharmaceutically acceptable salt or solvate thereof, normally in a pharmaceutical composition in admixture with a pharmaceutical carrier or vehicle, is administered to a patient in need of said treatment at a daily dose that is equivalent to from 0.375 mg to 45 mg, from 1.5 mg to 45 mg, from 3 mg to 45 mg, from 5 mg to 45 mg, from more than 6 mg to 45 mg and from 6.5 mg to 45 mg of pramipexole dihydrochloride monohydrate, in some cases from 1.5 mg to 20 mg, advantageously from 3 mg to 20 mg, preferably from 5 mg to 20 mg of pramipexole dihydrochloride monohydrate. In said method (or use) pramipexole is administered to said patient in combination with a 5HT3-antagonist.

According to a particular embodiment, in said method (or use), said pramipexole or pharmaceutically acceptable salt thereof is pramipexole dihydrochloride monohydrate, that is orally administered to said patient at a daily dose of from 1.5 mg to 20 mg, advantageously from 3 mg to 20 mg, normally from 5 mg to 20 mg. According to this embodiment, in said method (or use) said pramipexole or pharmaceutically acceptable salt thereof is administered to said patient in combination with said 5HT3-antagonist, administered by any administration route.

Preferably, in the method (or use) for treating a MDD in a patient according to the present invention, said 5HT3-antagonist, in said combination, is selected from the group consisting of ondansetron or a pharmaceutically acceptable salt thereof, administered at a daily dose equivalent to from 2 mg to 32 mg of ondansetron base, and dolasetron and pharmaceutically acceptable salts thereof, administered at a daily dose equivalent to from 75 mg to 200 mg of dolasetron mesylate; and said pramipexole or pharmaceutically acceptable salt thereof is administered at a daily dose equivalent to from 0.375 mg to 45 mg, in particular from 1.5 mg to 45 mg, from 3 mg to 45 mg, from 5 mg to 45 mg, from more than 6 mg to 45 mg and from 6.5 mg to 45 mg of pramipexole dihydrochloride monohydrate.

Normally, in said method (or use), said 5HT3-antagonist is ondansetron or a pharmaceutically acceptable salt thereof, at an effective daily dose (in ondansetron) of from 4 mg to 32 mg, administered in combination with said pramipexole or a pharmaceutically acceptable salt or solvate thereof, at an effective daily dose (in pramipexole dihydrochloride monohydrate) of from 1.5 mg to 20 mg, advantageously from 3 mg to 20 mg, preferably from 5 mg to 20 mg.

For their administration for the treatment of MDDs, said pramipexole or pharmaceutically acceptable salt or solvate thereof and said 5HT3-antagonist are each formulated in a pharmaceutical composition in admixture with a pharmaceutical carrier or vehicle. In particular, in said combination, said 5HT3-antagonist is formulated in a pharmaceutical composition in dosage unit form comprising, as an active ingredient, an effective amount per unit form of said 5HT3-antagonist in admixture with a pharmaceutical carrier or vehicle; and, respectively, said pramipexole or a pharmaceutically acceptable salt or solvate thereof is also formulated in a pharmaceutical composition in dosage unit form comprising, as an active ingredient, an effective amount of said pramipexole or a pharmaceutically acceptable salt or solvate thereof in admixture with a pharmaceutical carrier or vehicle.

More particularly, in said combination, said 5HT3-antagonist is formulated in a pharmaceutical composition in dosage unit form comprising said 5HT3-antagonist in an amount per unit form of from 0.1 mg to 300 mg, in admixture with a pharmaceutical carrier or vehicle; and said pramipexole or pharmaceutically acceptable salt thereof is formulated in a pharmaceutical composition in dosage unit form comprising said pramipexole or pharmaceutically acceptable salt thereof in an amount per unit form equivalent to from 0.125 mg to 45 mg of pramipexole dihydrochloride monohydrate, in admixture with a pharmaceutical carrier or vehicle.

Preferably, in said combination said 5HT3-antagonist in said composition is selected from the group consisting of ondansetron and pharmaceutically acceptable salt or solvate thereof, in an amount per unit form equivalent to from 2 mg to 32 mg of ondansetron base, and dolasetron and pharmaceutically acceptable salt or solvate thereof, in an amount per unit form equivalent to from 25 mg to 200 mg of dolasetron mesylate.

Pramipexole is preferably present, in said composition, in an amount per unit form equivalent to from 5 mg to 45 mg or from 6.5 mg to 45 mg, normally from 5 mg to 20 mg or from 6.5 mg to 20 mg of pramipexole dihydrochloride monohydrate.

The pharmaceutical compositions thus obtained are concurrently or sequentially administered to a patient suffering from a MDD.

Said pramipexole or pharmaceutically acceptable salt or solvate thereof and said 5HT3-antagonist may also be formulated together in a fixed-dose combination consisting of a pharmaceutical composition comprising said pramipexole or pharmaceutically acceptable salt or solvate thereof and said 5HT3-antagonist, in admixture with a pharmaceutical carrier or vehicle.

Normally, in the method (or use) of the present invention, said combination is a fixed-dose combination consisting of a pharmaceutical composition in dosage unit form comprising an effective amount per unit form of said 5HT3-antagonist, and an effective amount per unit form of said pramipexole or a pharmaceutically acceptable salt thereof, in admixture with a pharmaceutical carrier or vehicle.

The fixed-dose combinations assure the safe, concurrent administration of pramipexole or pharmaceutically acceptable salt or solvate thereof and of the 5HT3-antagonist.

As set forth above, when using a 5HT3-antagonist indicated for the prevention or treatment of postoperative nausea and vomiting or for the prevention of the chemotherapy-induced nausea and vomiting, the amount per unit form of said 5HT3-antagonist is at least as high as the pediatric or adult dose approved for this indication. However, it may be up to 6 times said dose.

In the above fixed-dose combinations, the pramipexole dose/unit form, in pramipexole dihydrochloride monohydrate, is in a range selected from the group consisting of from 0.125 mg to 45 mg, from 3 mg to 45 mg, from more than 4.5 mg to 45 mg, from 5 mg to 45 mg, from more than 6 mg to 45 mg and from 6.5 mg to 45 mg. Normally said range is selected from the group consisting of from 0.125 mg to 20 mg, from 3 mg to 20 mg, from more than 4.5 mg to 20 mg, from 5 mg to 20 mg, from more than 6 mg to 20 mg, and from 6.5 mg to 20 mg; and the dose/unit form of the 5HT3-antagonist ranges from 1 μg to 300 mg.

If the 5HT3-antagonist is ondansetron or a pharmaceutically acceptable salt or solvate thereof, its dose/unit form (in ondansetron) is from 2 mg to 32 mg, normally from 4 mg to 32 mg.

If the 5HT3-antagonist is dolasetron or a pharmaceutically acceptable salt or solvate thereof, its dose/unit form (in dolasetron mesylate) is from 1.5 mg to 200 mg. If said pramipexole or pharmaceutically acceptable salt thereof is pramipexole dihydrochloride monohydrate, the dose-range per oral IR-unit form, depending on safety and tolerability (in combination with the 5HT3-antagonist) is selected from the group consisting 0.125 mg to 22.5 mg, from 1.5 mg to 22.5 mg, from 3 mg to 22.5 mg, from more than 4.5 mg to 22.5 mg, from 5 mg to 22.5 mg, from more than 6 mg to 22.5 mg, and from 6.5 mg to 22.5 mg, normally from 1.5 mg to 10 mg, from 3 mg to 10 mg, from more than 4.5 mg to 10 mg, from 5 mg to 10 mg, from more than 6 mg to 10 mg, and from 6.5 mg to 10 mg. If the 5HT3-antagonist is ondansetron hydrochloride dihydrate, the ondansetron dose per oral IR unit form, in combination with pramipexole dihydrochloride monohydrate, will be equivalent to from 2 mg to 16 mg, normally from 4 mg to 16 mg of ondansetron base.

The dose/unit form of pramipexole or pharmaceutically acceptable salt thereof, in pramipexole dihydrochloride monohydrate, in an ER formulation, including slow-release compositions and transdermal therapeutic systems such as transdermal patches, will be in a range selected from the group consisting of from 1.5 mg to 45 mg, from 3 mg to 45 mg, from more than 4.5 mg to 45 mg, from 5 mg to 45 mg, from more than 6 mg to 45 mg, and from 6.5 mg to 45 mg, normally from 1.5 mg to 20 mg, from 3 mg to 20 mg, from more than 4.5 mg to 20 mg, from 5 mg to 20 mg, from more than 6 mg to 20 mg, and from 6.5 mg to 20 mg, depending on the tolerability (in combination with the 5HT3-antagonist).

If the 5-HT3 antagonist is ondansetron or a pharmaceutically acceptable salt or solvate thereof, the dose/ER-unit form (in ondansetron) will range from 8 mg to 32 mg.

If the 5-HT3 antagonist is dolasetron or a pharmaceutically acceptable salt or solvate thereof, the dose/unit form (in dolasetron mesylate) in combination with pramipexole, at the above doses/unit form, will range from 1.5 mg to 200 mg.

Second Aspect of the Invention

A second aspect of the present invention provides the use of said 5HT3-antagonist for the preparation of a medicament consisting of a pharmaceutical composition comprising, as an active ingredient, said 5HT3-antagonist, in admixture with a pharmaceutical carrier or vehicle, for the treatment of a MDD in combination with an effective daily dose of pramipexole or a pharmaceutically acceptable salt or solvate thereof.

A first embodiment of this second aspect of the invention provides the use of said 5HT3-antagonist for the preparation of a medicament consisting of a pharmaceutical composition comprising, as an active ingredient, said 5HT3-antagonist, in admixture with a pharmaceutical carrier or vehicle, for the treatment of a MDD in combination with pramipexole or a pharmaceutically acceptable salt or solvate thereof, also in a pharmaceutical composition in admixture with a pharmaceutical carrier or vehicle.

Said pramipexole daily doses may be much higher than the pramipexole dihydrochloride monohydrate maximum daily dose recommended for the treatment of symptoms of PD.

A second embodiment of this second aspect provides the use of said 5HT3-antagonist for the preparation of a medicament consisting of a pharmaceutical composition in dosage unit form comprising an effective dose per unit form of said 5HT3-antagonist, in admixture with a pharmaceutical carrier, for the treatment of a MDD in combination with pramipexole or a pharmaceutically acceptable salt or solvate thereof in doses, in pramipexole dihydrochloride monohydrate, at least as high as a dose approved for the symptomatic treatment of PD.

In particular, the 5HT3-antagonist is formulated in a pharmaceutical composition comprising said 5HT3-antagonist in an amount per unit form of from 1 μg to 300 mg, from 0.1 mg to 300 mg or from 1 mg to 300 mg, in admixture with a pharmaceutical carrier or vehicle.

A preferred 5HT3-antagonist in said pharmaceutical composition, for its indication for the treatment of a MDD in combination with said pramipexole, is selected from the group consisting of azasetron and pharmaceutically acceptable salts and solvates thereof, in particular its hydrochloride, in an amount/unit form equivalent to from 5 mg to 10 mg of azasetron hydrochloride; dolasetron and pharmaceutically acceptable salts and solvates thereof, in particular its mesylate monohydrate, in an amount/unit form equivalent to from 20 mg to 200 mg of dolasetron mesylate; granisetron and pharmaceutically acceptable salts and solvates thereof, in particular its hydrochloride, in an amount/unit form equivalent to from 0.5 mg to 2 mg granisetron base; ondansetron and pharmaceutically acceptable salts and solvates thereof, in particular its hydrochloride dihydrate, in an amount/unit form equivalent to from 2 mg to 32 mg, normally from 2 mg to 16 mg of ondansetron base; palonosetron and pharmaceutically acceptable salts and solvates thereof, in particular its hydrochloride, in an amount/unit form equivalent to from 0.1 mg to 2 mg, normally from 0.25 mg to 0.5 mg palonosetron base; ramosetron and pharmaceutically acceptable salts and solvates thereof, in particular its hydrochloride, in an amount/unit form equivalent to from 2.5 μg to 100 μg of ramosetron hydrochloride; and tropisetron and pharmaceutically acceptable salts and solvates thereof, in particular its hydrochloride, in an amount/unit form equivalent to from 2.5 mg to 5 mg tropisetron base.

Said 5HT3-antagonist in said pharmaceutical composition comprising, as an active ingredient, said 5HT3-antagonist in admixture with a pharmaceutical carrier or vehicle, is administered, concurrently or sequentially, in combination with pramipexole, also in a pharmaceutical composition, in admixture with a pharmaceutical carrier or vehicle, for the treatment of a MDD in a patient in need of said treatment. Said pharmaceutical compositions and the daily doses are illustrated above, in "The pramipexole" section.

These pharmaceutical compositions, constantly used in combination each other, for the first time allow the use of pramipexole high doses for a substantial and efficacious treatment of a patient suffering from a MDD. In fact, a pharmaceutical composition as described according to this second aspect of the invention allows for the safe treatment of a patient suffering from a MDD, in combination with a pramipexole daily dose of from 0.375 mg to 45 mg, especially from more than 4.5 mg to 45 mg, normally from 5 mg to 45 mg, from more than 6 mg to 45 mg or from 6.5 mg to 45 mg, thus alleviating and even resolving the depressive state of said patients. In certain cases, said pramipexole daily dose is from more than 4.5 mg to 20 mg, from 5 mg to 20 mg, from more than 6 mg to 20 mg or from 6.5 mg to 20 mg.

In the treatment of MDD, the 5HT3-antagonist and pramipexole are used in combination and the two active components may be co-administered simultaneously or sequentially, or in a fixed dose combination including a pharmaceutical composition comprising the 5HT3-antagonist and 6-propylamino-4,5,6,7-tetrahydro-1,3-benzothiazole-2-amine, together in admixture with a pharmaceutically acceptable carrier or vehicle.

The 5HT3-antagonist and pramipexole can be administered separately or together in any conventional oral or parenteral dosage unit form such as capsule, tablet, powder, cachet, suspension, solution, or transdermal device.

In the case of separate (concurrent or sequential) administration of said 5HT3-antagonist, in an effective amount per unit form, and of said pramipexole, in an effective amount per unit form, each of them can be packaged in a kit comprising said 5HT3-antagonist, in admixture with a pharmaceutical carrier or vehicle, in a container; and said pramipexole, in admixture with a pharmaceutical carrier or vehicle, in another, separate container.

In the case of a concurrent administration, as also set forth above, said 5HT3-antagonist and said pramipexole may be formulated together in a fixed-dose combination consisting of a pharmaceutical composition in dosage unit form comprising an effective amount per unit form of said 5HT3-antagonist and an effective amount per unit form of said pramipexole or a pharmaceutically acceptable salt thereof, in admixture with a pharmaceutical carrier or vehicle.

A third embodiment of this second aspect of the invention provides the use of said 5HT3-antagonist for the preparation of a medicament for the treatment of a MDD, said medicament being a fixed-dose combination consisting of a pharmaceutical composition comprising, as an active ingredient, said 5HT3-antagonist and, as a second active ingredient, pramipexole or a pharmaceutically acceptable salt or solvate thereof, in admixture with a pharmaceutical carrier or vehicle.

According to this third embodiment of this second aspect of the invention, said fixed-dose combination consists of a pharmaceutical composition comprising (a) said 5HT3-antagonist; and (b) pramipexole or a pharmaceutically acceptable salt or solvate thereof, in an amount per unit form (in pramipexole dihydrochloride monohydrate) at least as high as an amount per unit form approved for the treatment of PD, in admixture with a pharmaceutical carrier or vehicle, for use for the treatment of MDD.

Advantageously, according to this third embodiment of this second aspect of the invention, said fixed-dose combination consists of a pharmaceutical composition in dosage unit form comprising (a) said 5HT3-antagonist, in an amount/unit form at least at least as high as an amount/unit form approved for the prevention of chemotherapy-induced nausea and vomiting; and (b) pramipexole or a pharmaceutically acceptable salt or solvate thereof, in an amount/unit form (in pramipexole dihydrochloride monohydrate) at least as high as an amount/unit form approved for the treatment of PD, in admixture with a pharmaceutical carrier or vehicle, for the treatment of MDD.

In general, in the above pharmaceutical composition said 5HT3-antagonist is present in an amount of from 1 μg to 300 mg and said pramipexole is present in an amount of from 0.125 mg to 45 mg.

If the 5HT3-antagonist is selected from among those indicated for the prevention or treatment of postoperative nausea and vomiting or for the prevention of the chemotherapy-induced nausea and vomiting, said 5HT3-antagonist is present in said composition in an amount/unit form at least at least as high as an amount/unit form shown to be effective in or approved for the prevention or treatment of postoperative nausea and vomiting or for the prevention of the chemotherapy-induced nausea and vomiting, and up to 6 times said dose. Said 5HT3-antagonists and their amounts per unit form in pharmaceutical compositions for use in the treatment of MDD are illustrated in the "The 5HT3-antagonist" section.

In these fixed-dose combinations, the pramipexole dose/unit form, in pramipexole dihydrochloride monohydrate, normally ranges from 0.125 mg to 20 mg, advantageously from 3 mg to 20 mg, preferably from 5 mg to 20 mg, from more than 6 mg to 20 mg or from 6.5 mg to 20 mg; and the dose/unit form of the 5HT3-antagonist ranges from 1 μg to 300 mg.

If the 5HT3-antagonist is ondansetron or a pharmaceutically acceptable salt or solvate thereof, its dose/unit form (in ondansetron) is from 2 mg to 32 mg, normally from 4 mg to 32 mg.

If the 5HT3-antagonist is dolasetron or a pharmaceutically acceptable salt or solvate thereof, its dose/unit form (in dolasetron mesylate) is from 1.5 mg to 200 mg.

An advantageous fixed-dose combination consists of a pharmaceutically composition in dosage unit form comprising (a) a 5HT3-antagonist selected from the group consisting of alosetron or a pharmaceutically acceptable salt or solvate thereof, in particular its hydrochloride, in an amount/unit dose (in alosetron) of from 0.25 mg to 2 mg; azasetron or a pharmaceutically acceptable salt or solvate thereof, in particular its hydrochloride, in an amount/unit dose of from 5 mg to 10 mg; dolasetron or a pharmaceutically acceptable salt or solvate thereof, in particular its mesylate monohydrate, in an amount/unit dose (in dolasetron mesylate) of from 25 mg to 200 mg; granisetron or a pharmaceutically acceptable salt or solvate thereof, in particular its hydrochloride, in an amount/unit dose equivalent to from 0.5 mg to 2 mg granisetron base; ondansetron or a pharmaceutically acceptable salt or solvate thereof, in particular its hydrochloride dihydrate, in an amount/unit dose equivalent to from 2 mg to 32 mg of ondansetron base; palonosetron or a pharmaceutically acceptable salt or solvate thereof, in particular its hydrochloride, in an amount/unit dose equivalent to from 0.25 mg to 0.5 mg palonosetron base; ramosetron or a pharmaceutically acceptable salt or solvate thereof, in particular its hydrochloride, in an amount/unit dose of from 50 μg to 40 mg; and tropisetron or a pharmaceutically acceptable salt or solvate thereof, in particular its hydrochloride, in an amount/unit dose equivalent to from 2.5 mg to 5 mg tropisetron base; and (b) pramipexole or a pharmaceutically acceptable salt or solvate thereof, in an amount equivalent to from 0.125 mg to 45 mg, preferably from 5 mg to 45 mg, from more than 6 mg to 45 mg, or from 6.5 mg to 45 mg, and normally equivalent to a range selected from the group consisting of from 0.125 mg to 20 mg, from 3 mg to 20 mg, from more than 4.5 mg to 20 mg, from 5 mg to 20 mg, from more than 6 mg to 20 mg and from 6.5 mg to 20 mg, of pramipexole dihydrochloride monohydrate, in admixture with a pharmaceutical carrier or vehicle.

According to an embodiment, said advantageous composition comprises, as active ingredients, (a) a 5HT3-antagonist selected from the group consisting of ondansetron or a salt or solvate thereof, in an amount (in ondansetron base) of from 2 mg to 32 mg; and dolasetron, in an amount (in dolasetron mesylate) from 25 mg to 200 mg; and (b) pramipexole or a pharmaceutically acceptable salt thereof, in an amount (in pramipexole dihydrochloride monohydrate) of from 0.125 mg to 45 mg, in admixture with a pharmaceutical carrier or vehicle.

Said advantageous composition preferably comprises, as Component (b) pramipexole or a pharmaceutically acceptable salt thereof, in an amount (in pramipexole dihydrochloride monohydrate) selected from the group consisting of from 3 mg to 45 mg, from 5 mg to 45 mg, from more than 6 mg to 45 mg, and from 6.5 mg to 45 mg.

A 5HT3-antagonist/pramipexole fixed-dose combination, normally for use in the treatment of MDD, consists of a pharmaceutical composition comprising a 5HT3-antagonist selected from the group consisting of ondansetron or a pharmaceutically acceptable salt or solvate thereof, in an amount corresponding to from 2 mg to 32 mg of ondansetron base, as Component (a); and pramipexole or a pharmaceutically acceptable salt or solvate thereof, in an amount that is equivalent to from 0.125 mg to 20 mg, advantageously from 3 mg to 20 mg, preferably from 5 mg to 20 mg, from more than 6 mg to 20 mg or from 6.5 mg to 20 mg, of pramipexole dihydrochloride monohydrate, as Component (b), in admixture with a pharmaceutical carrier or vehicle.

Herein, the pramipexole doses/unit forms include low doses that can be used especially in the case of the titration of the pramipexole daily dose or in the less frequent case of use in the treatment of pediatric depressed patients.

The Formulations

In the pharmaceutical compositions of the present invention for oral, subcutaneous, intravenous, transdermal or topical administration, the active ingredients are preferably administered in the form of dosage units, in admixture with the classic pharmaceutical carriers or vehicles.

The pharmaceutical compositions may be formulated in oral forms such as tablets or gelatin capsules wherein the 5HT3-antagonist or pramipexole or both the active ingredients are in admixture with a carrier or vehicle that may include a diluent, such as cellulose, dextrose, lactose, mannitol, sorbitol or sucrose; a lubricant, such as, acid, calcium or magnesium stearate, polyethylene glycol, silica, or talc; and if needed, a binder such as magnesium aluminum silicate, gelatin, methylcellulose, sodium carboxymethylcellulose, or polyvinylpyrrolidone.

Said oral forms may be tablets coated with sucrose or with various polymers; or, alternatively, the tablets can be manufactured by using carriers such as acrylic and methacrylic acid polymers and copolymers; cellulose derivatives such as hydroxypropylethylcellulose; or other appropriate materials, to have a prolonged or delayed activity by progressively releasing a predetermined quantity of 5HT3-antagonist or of pramipexole (or of a pharmaceutically acceptable salt or solvate thereof), or of both the active ingredients. The oral formulations can also be in form of capsules allowing the extended release the pramipexole (or pharmaceutically acceptable salt or solvate thereof), or of 5HT3-antagonist, or of both the active ingredients.

The pharmaceutical compositions may also be formulated in TTS, such as a patch formulation wherein the active ingredient or the mixture of the active ingredients may comprise adjuvants such as D-sorbitol, gelatin, kaolin, methyl paraben, polysorbate 80, propylene glycol, propyl paraben, povidone, sodium carboxymethylcellulose, sodium polyacrylate, tartaric acid, titanium dioxide, and purified water. A patch formulation may also contain skin permeability enhancer such as lactate esters (e.g., lauryl lactate), triacetin or diethylene glycol monoethyl ether.

In the above pharmaceutical compositions, the preferred pramipexole or pharmaceutically acceptable salt or solvate thereof active ingredient is pramipexole base or its dihydrochloride monohydrate and the preferred 5HT3-antagonist active ingredient is ondansetron base or its hydrochloride dihydrate, or dolasetron base or its mesylate monohydrate.

For the intended use in the treatment of MDDs in combination with pramipexole, the 5HT3-antagonist is formulated in a pharmaceutical composition, wherein said 5HT3-antagonist is in admixture with a pharmaceutical carrier or vehicle.

The dosage, i.e. the amount of active ingredient in a single dose to be administered to the patient, can vary widely depending on the age, weight, and the health condition of the patient. This dosage, in a pharmaceutical composition in dosage unit form as illustrated herein above, includes the administration of a single dose from 1 μg to 300 mg according to the potency of each 5HT3-antagonist and the age of the patient, and a single dose of pramipexole or a pharmaceutically acceptable salt thereof that is equivalent to from 0.125 mg to 45 mg, normally from 0.125 mg to 20 mg, advantageously from 3 mg to 20 mg, preferably from 5 mg to 20 mg or from 6.5 mg to 20 mg of pramipexole dihydrochloride monohydrate, according to the age of the patient, from one to three times a day by intravenous, subcutaneous, oral, or transcutaneous administration, according to the strength of the doses of the each of the active ingredients. If the 5HT3-antagonist is ondansetron hydrochloride dihydrate, said dosage (single dose) ranges from 4 mg to 16 mg (in ondansetron base); and, if the pramipexole or a pharmaceutically acceptable salt thereof is pramipexole dihydrochloride monohydrate, said dosage (single dose) ranges from 0.125 mg to 45 mg, from 3 mg to 45 mg, from 5 mg to 45 mg, from more than 6 mg or from 6.5 mg to 45 mg, normally from 0.125 mg to 20 mg, advantageously from 3 mg to 20 mg, preferably from 5 mg to 20 mg or from 6.5 mg to 20 mg.

Ondansetron may also be administered via a transdermal drug delivery system (TDDS). "Transdermal drug delivery system" provides transdermal delivery using transdermal drug formulations and transdermal patches incorporating such transdermal drug formulations. For example, the transdermal drug delivery system may include a composition in form of a patch, a cream, a gel, a lotion or a paste comprising a 5HT3-antagonist (such as ondansetron). Examples of transdermal formulations may include, but are not limited, to those as described in U.S. Pat. No. 6,562,368, a transdermal gel formulation as described in U.S. Pat. Nos. 7,029,694; 7,179,483; 8,241,662 and US 2009/0018190, a transdermal or transmucosal pharmaceutical formulation, that can be utilized for topical or transdermal application, such that solutions, creams, lotions, sprays, ointment, gels, aerosols and patch drug deliveries as described in WO 2005/039531, US2007/022379, US 2010/0216880, US 2014/0037713 and U.S. Pat. No. 8,652,491, a transdermal absorption preparation as described in WO2013/061969 and US 2014/0271796, the disclosures of which are herein incorporated by reference in their entirety. The transdermal patches may also include, but are not limited to, a patch pump having an in-dwelling rigid catheter with flexible features and/or a flexible catheter attachment as described in U.S. Pat. No. 9,782,536, a selectively activatable patch pump as described in U.S. Pat. No. 9,724,462, a patch pump attached to a wireless communication system as described in U.S. Pat. No. 9,623,173, a conformable patch pump as described in U.S. Pat. No. 9,616,171, an infusion pump as described in U.S. Pat. No. 8,915,879, a portable infusion drug delivery as described in U.S. Pat. No. 8,480,649, a micropump as described in U.S. Pat. No. 8,282,366, and a patch pump as described in U.S. Pat. No. 7,828,771; the disclosures of which are herein incorporated by reference in their entirety. Other transdermal patches may include, but are not limited to, a patch in which oxybutynin is incorporated in an adhesive agent layer composition comprising the acrylic-based polymer as the adhesive base agent, and the acrylic-based polymer is a copolymer of polymethyl methacrylate with a polyacrylate as described in U.S. Pat. No. 8,802,134, a patch consisting of a support layer and of an adhesive agent layer arranged on the at least one surface of the support layer as described in U.S. Pat. No. 8,877,235, a patch using a monoglyceride or a mixture of monoglycerides of fatty acids as skin permeation-enhancer as described in U.S. Pat. Nos. 5,441,740 and 5,500,222, a patch for using a monoglyceride or a mixture of monoglycerides plus a lactate ester as skin permeation-enhancer as described in U.S. Pat. Nos. 5,686,097; 5,747,065; 5,750,137 and 5,900,250, a patch with a non-rate controlling tie layer on the skin-proximal surface of the reservoir, not affecting the drug release as described in U.S. Pat. Nos. 5,614,211 and 5,635,203, a patch using triacetin as permeation enhancer as described in U.S. Pat. Nos. 5,212,199, 5,227,169, 5,601,839 and 5,834,010, a patch with a matrix mass in the form of a layer which is self-adhesive, and in which the matrix mass consists of ammonium-group-containing (meth)acrylate copolymers as described in U.S. Pat. No. 6,555,129, a transdermal patch as described in U.S. Pat. Nos. 6,743,441; 7,081,249; 7,081,250; 7,081,251; 7,081,252 and 7,087,241; the disclosures of which are herein incorporated by reference in their entirety. Preferably, the transdermal drug delivery system is a patch, a patch pump, an infusion pump, or a micropump.

The pharmaceutical compositions of the present invention are formulated with the classic excipients suitable for different ways of administration. Particularly advantageous are the formulations in the form of tablets, multi-score tablets, coated tables, orally disintegrating tablets, extended release tablets, hard or soft capsules, extended-release capsules, patches for transdermal administration, liquid oral solutions, syrups or suspensions in a predetermined unit form, and vials for the intravenous or subcutaneous administration.

Thus, for example, a pharmaceutical composition according to the present invention to be chronically administered in combination with pramipexole or a pharmaceutically acceptable salt or solvate thereof, in an amount per unit dose (in pramipexole dihydrochloride monohydrate) of from 0.125 mg to 45 mg, from 3 mg to 45 mg, from 5 mg to 45 mg, from more than 6 mg to 45 mg or from 6.5 mg to 45 mg, normally from 0.125 mg to 20 mg, advantageously from 3 mg to 20 mg, preferably from 5 mg to 20 mg or from 6.5 mg to 20 mg, to be administered at a daily dose of from 1.5 mg to 45 mg, advantageously from 3 mg to 45 mg, preferably from 5 mg to 45 mg or from 6.5 mg to 45 mg, normally from 1.5 mg to 20 mg, advantageously from 3 mg to 20 mg, preferably from 5 mg to 20 mg or from 6.5 mg to 20 mg, may comprise alosetron hydrochloride, in an amount/unit dose (in alosetron) of from 0.25 mg to 2 mg to be administered at a daily dose of from 0.25 mg to 3 mg; azasetron hydrochloride, in an amount/unit dose of from 5 mg to 10 mg to be administered at a daily dose of from 15 mg to 20 mg; dolasetron mesylate monohydrate, in an amount/unit dose (in dolasetron mesylate) of from 25 mg to 200 mg to be administered at a daily dose of from 75 mg to 200 mg; granisetron hydrochloride, in an amount/unit dose equivalent to from 0.5 mg to 2 mg granisetron base, to be administered at a daily dose of from 1.5 mg to 8 mg; ondansetron hydrochloride dihydrate, in an amount/unit dose equivalent to from 2 mg to 8 mg ondansetron base, to be administered at a daily dose of from 6 mg to 32 mg; palonosetron hydrochloride, in an amount/unit dose equivalent to from 0.25 mg to 0.5 mg palonosetron base, to be administered at a daily dose of from 0.75 to 2 mg; ramosetron hydrochloride, in an amount/unit dose of from 50 μg to 20 mg to be administered at a daily dose of from 75 μg to 40 mg; or tropisetron hydrochloride, in an amount/unit dose equivalent to from 2.5 mg to 5 mg tropisetron base, to be administered at a daily dose of from 7.5 to 20 mg.

In the case of pediatric or obese patients, the 5HT3-antagonist daily dose may be decided on the basis of the body weight. Thus, for example, azasetron hydrochloride may be administered at a daily dose of 0.4-0.5 mg/kg, dolasetron mesylate may be administered at a daily dose of 9-9.5 mg/kg, granisetron hydrochloride may be administered at a daily dose of 0.09-0.11 mg/kg, ondansetron hydrochloride dihydrate may be administered at a daily dose of 0.45-0.55 mg/kg, palonosetron hydrochloride may be administered at a daily dose of 0.03 mg/kg and tropisetron hydrochloride may be administered at a daily dose of 0.5-0.6 mg/kg.

EXAMPLE 1

The ability of the 5HT3-antagonists to prevent the gastro-intestinal (GI) adverse effects (AEs) of pramipexole in humans was tested.

A Phase I study was conducted in subjects receiving a single oral dose of pramipexole dihydrochloride monohydrate ("pramipexole") with or without a single oral dose of ondansetron hydrochloride dihydrate ("ondansetron"). The study was single center, single-blind study.

The objective of the study was to demonstrate that ondansetron could safely attenuate the gastro-intestinal side effects of pramipexole given in doses equivalent or higher than those approved in the treatment of Parkinson's Disease or shown in clinical trials to be effective in the treatment of depression.

To be enrolled in the study, participants the following inclusion/exclusion key criteria:

Key Inclusion Criteria

1. Male and female subjects aged 20-45 years old both ages included.
2. Females of childbearing potential must agree to be abstinent or else use any two of the following medically acceptable forms of contraception from the Screening Period through 14 days after the study Exit Visit: condom with spermicidal jelly, diaphragm or cervical cap with spermicidal jelly, or intrauterine device (IUD). A female whose male partner has had a vasectomy must agree to use one additional form of medically acceptable contraception. Subjects must agree to practice the above birth control methods for 14 days after the final visit as a safety precaution.
3. Females of non-childbearing potential, defined as surgically sterile (status post-hysterectomy, bilateral oophorectomy, or bilateral tubal ligation) or post-menopausal for at least 12 months, do not require contraception during the study. The reason must be documented in the source documents.
4. Males with female partners of childbearing potential must agree to use a highly effective, medically acceptable form of contraception from the Screening Period through 14 days after the study Exit Visit. Males with female partners of childbearing potential who themselves are surgically sterile (status post vasectomy) must agree to use condoms with spermicide over the same period of time. Male subjects must agree to practice the above birth control methods for 14 days after the final visit as a safety precaution.
5. Subjects must be in good health as determined by their medical history including personal and family psychiatric history and results of physical examination, electrocardiogram (ECG), vital signs, and laboratory tests. A subject with a medical abnormality may be included only if the investigator or designee considers that the abnormality will not introduce significant additional risk to the subject's health or interfere with study objectives. 6. Subjects must be able to clearly and reliably communicate changes in their medical condition.
7. Subjects with a body mass index (BMI) between 19.0 and 32.0 kg/m2 (both inclusive).
8. Subjects able to swallow multiple pills or capsules simultaneously.
9. Subjects must have signed an informed consent form indicating that they understand the purpose of and procedures required for the study and are willing to participate in the study and comply with the study procedures and restrictions.

Key Exclusion Criteria:

The criteria for exclusion of a subject from enrollment in the study were as follows:

1. Any clinically relevant acute or chronic diseases which could interfere with the subjects' safety during the trial, expose them to undue risk, or interfere with the study objectives.
2. History or presence of gastrointestinal, hepatic, or renal disease or other condition known to interfere with the absorption, distribution, metabolism or excretion of the study drugs.
3. History of substance abuse, known drug addiction, or positive test for drugs of abuse or alcohol.
4. History of drug or other significant allergy.
5. Known hypersensitivity to pramipexole, or to ondansetron or similar serotonin receptor antagonists, or to aprepitant or similar Substance P/NK1 receptor antagonists.
5. History of and/or current QT interval prolongation, congenital long QT syndrome, electrolyte abnormalities (e.g., hypokalemia or hypomagnesemia), congestive heart failure, bradyarrhythmias or other medicinal products that lead to QT prolongation or 1st degree AV block at Screening, Day-1, or pre-dose, ≥450 QTcF for males and ≥470 QTcF for females.
7. Treatment with centrally active drugs or antiemetics, within 1 months of study entry.
8. Tobacco or nicotine users (except subjects who stopped using tobacco or nicotine 1 year or more before enrollment in the study).
9. Excessive daily consumption of xanthines containing drinks (i.e. >500 mg/day of caffeine).
10. Subjects unwilling to curtail prolonged intensive physical exercise during the study conduct (from the Screening visit until the last dose of study drug).
11. Positive test result for hepatitis B surface antigen, hepatitis C antibody.
12. Positive test result for HIV 1 or 2 serology.
13. Likely to need any medical or dental treatment during the study period.
14. Use of any prescription or over-the-counter medication within 14 days prior to admission on Day-1. In addition any medications with central effects are prohibited for a period equal to 5 times the drug half-life prior to admission (Day −1), should this period be longer than 14 days.
15. Subjects unlikely to co-operate during the study, and/or be questionably compliant in the opinion of the investigator.

16. Subjects unable to be contacted in case of an emergency.
17. Intake of an investigational drug within 30 days of study entry. 18. Show evidence of suicidal ideation within the last 6 months as assessed by the C-SSRS (Columbia Suicide Severity Rating Scale) at Screening.

Following enrollment in the study, participants received single increasing oral doses of pramipexole given once daily in the morning (Period 1 of the study). The starting dose of pramipexole was 0.5 mg and the dose was increased daily by 0.5 mg increments. Once a subject had reached his/her first intolerable dose (FID-1), upward dose escalation was discontinued. First intolerable dose (FID) was defined as:

one (1) episode of vomiting; or

Two (2) episodes of retching, or

One (1) episode of severe nausea (Grade 3; defined as nausea interfering with activities of daily living or inadequate oral caloric or fluid intake; tube feeding, total parenteral nutrition or hospitalization indicated) lasting more than 1 hour, or Three (3) consecutive episodes at every 4 hour ratings of moderate nausea (Grade 2; defined as subjectively symptomatic, but not interfering with activities of daily living), or One (1) episode of moderate diarrhea (Grade 2; defined as 4-6 stools more than at baseline).

When a subject reached FID-1 on pramipexole alone, the subject was washed out for at least 5 days, and then entered Period 2 of the study during which the subject received single daily oral doses of pramipexole starting at 0.5 mg and titrated upward by 0.5 mg increments, together with oral ondansetron hydrochloride dihydrate (10 mg, equivalent to 8 mg ondansetron base) until subjects again reached an intolerable dose defined as above. The FID on oral pramipexole plus oral ondansetron was referred to as FID-2.

If a subject reached FID-2 during Period 2 at the same or lower dose than FID-1, and providing the investigator judged there were no safety issues and the subject was consenting, the subject received the same dose of pramipexole as the FID-2 dose together with a higher dose of oral ondansetron hydrochloride dihydrate (20 mg, equivalent to 16 mg ondansetron base) on the next day and the protocol specified that said subject should continue with the remainder of the dose titration with the higher dose of oral ondansetron hydrochloride dihydrate (20 mg, equivalent to 16 mg ondansetron base) until they reach the intolerable dose (FID2+). All other provisions of the protocol remained unchanged. Assessments were the same as those planned for the dose escalation day.

On each study day, subjects were followed up for up to 8 hours following drug administration for AEs, vital signs, ECGs. In addition, a laboratory panel was taken at screening and at the end of the study.

Three subjects were enrolled in the study. The following Table 1 summarizes the demographic characteristics of the subjects.

TABLE 1

Demographic Characteristics of Subjects Enrolled in the Study

| Subject ID | Gender | Age (years) | Baseline Weight (kg) |
|---|---|---|---|
| 1001 (019) | Female | 40 | 76.4 kg |
| 1005 (027) | Female | 30 | 54.8 kg |
| 1006 (001) | Male | 41 | 99.1 kg |
| 1007 (004) | Male | 38 | 64.9 kg |
| 1008 (008) | Male | 39 | 81.8 kg |

All subjects reached FID-1 (pramipexole alone) during the study. The dose limiting toxicity was gastro-intestinal adverse events in all 5 subjects. For all subjects FID-2 was higher than FID-1. During Period 2 of the study, 3 of the 5 subjects tolerated the maximum pramipexole dose allowed by the protocol of 6 mg and therefore these subjects did not reach FID-2 (pramipexole with ondansetron). In other words, concomitant administration of ondansetron with pramipexole prevented the occurrence of dose-limiting gastro-intestinal adverse events associated with high doses of pramipexole. Table 2 lists for each subject the values for FID-1 (on pramipexole alone) and FID-2 (on pramipexole+ondansetron).

TABLE 2

Listing of First Intolerable Doses (FID) values

| Subject ID | FID-1 (Pramipexole alone) | FID-1 Dose Limiting Adverse Event | FID-2 Pramipexole + Ondansetron |
|---|---|---|---|
| 1001 | 2.5 mg | GI issues | >6.0 mg |
| 1005 | 2.0 mg | Retching | 3.0 mg |
| 1006 | 0.5 mg | Moderate nausea | 1.0 mg |
| 1007 | 4.5 mg | Severe nausea | >6.0 mg |
| 1008 | 1.5 mg | Vomiting | >6.0 mg |

As shown in the following Table 3, the Maximum Tolerated Dose (MTD) during Period 2 was higher than MTD during Period 1 in all subjects, and in 2 subjects MTD-2 was increased by more than 3-fold.

TABLE 3

Listing of Maximum Tolerated Doses (MTD)

| Subject ID | MTD-1 (Pramipexole alone) | Maximal Tolerated Dose Pramipexole + Ondansetron | MTD2/MTD1 |
|---|---|---|---|
| 1001 | 2.0 mg | >6.0 mg | >3.0 |
| 1005 | 1.5 mg | 2.5 mg | 1.67 |
| 1006 | NA (not tolerated at 0.5 mg) | 0.5 mg | >1.0 |
| 1007 | 4.0 mg | >6.0 mg | >1.5 |
| 1008 | 1.0 mg | >6.0 mg | >6 |

MTD: Maximum Tolerated Dose

Results showed that the co-administration of ondansetron with pramipexole allowed tolerable increases in the dose of pramipexole resulting in toleration of higher pramipexole doses than if pramipexole had been given alone.

In conclusion, the co-administration of oral high doses of ondansetron with pramipexole prevented the occurrence of gastro-intestinal AEs when pramipexole was given in doses as high as or higher than the recommended efficacious dose for the treatment of the symptoms of Parkinson's disease.

REFERENCES

Barone et al. 2010: Barone P, Poewe W, Albrecht S, Debieuvre C, Massey D, Rascol O, Tolosa E, Weintraub D. "*Pramipexole for the treatment of depressive symptoms in patients with Parkinson's disease: a randomised, double-blind, placebo-controlled trial*." Lancet Neurol. 2010 June; 9(6):573-80. doi: 10.1016/S1474-4452 (10) 70106-X. Epub 2010 May 7.

Corrigan et al. 2000: Corrigan M H, Denahan A Q, Wright C E, Ragual R J, Evans D L; Corrigan M H, Denahan A Q, Wright C E, Ragual R J, Evans D; "*Comparison of pramipexole, fluoxetine, and placebo in patients with major depression*"; Depress Anxiety. 2000; 11(2):58-65.

Cusin et al. 2013: Cusin C, Iovieno N, Iosifescu D V, Nierenberg A A, Fava M, Rush A J, Perlis R H. *A randomized, double-blind, placebo-controlled trial of pramipexole augmentation in treatment-resistant major depressive disorder*. J Clin Psychiatry. 2013 July; 74 (7).

Dell'Osso et al 2013: Dell'Osso B, Ketter T A. *Assessing efficacy/effectiveness and safety/tolerability profiles of adjunctive pramipexole in bipolar depression: acute versus long-term data*. Int Clin Psychopharmacol. 2013 November; 28(6):297-304.

de Sousa et al 2015: de Sousa R T, Zanetti M V, Brunoni A R, Machado-Vieira R. *Challenging Treatment-Resistant Major Depressive Disorder: A Roadmap for Improved Therapeutics*. Current Neuropharmacology, 2015, 13, 616-635.

Fawcett et al 2016: Fawcett J, Rush A J, Vukelich J, Diaz S H, Dunklee L, Romo P, Yarns B C, Escalona R. *Clinical Experience With High-Dosage Pramipexole in Patients With Treatment-Resistant Depressive Episodes in Unipolar and Bipolar Depression*. Am J Psychiatry. 2016 Feb. 1; 173(2):107-11.

Goldberg et al 2004: Goldberg J F, Burdick K E, Endick C J. *Preliminary randomized, double-blind, placebo-controlled trial of pramipexole added to mood stabilizers for treatment-resistant bipolar depression*. Am J Psychiatry. 2004 March; 161(3):564-6.

Hori et al. 2012: Hori H, Kunugi H. *The efficacy of pramipexole, a dopamine receptor agonist, as an adjunctive treatment in treatment-resistant depression: an open-label trial*. ScientificWorldJournal. 2012; 2012:372474.

Kleeblatt et al 207: Kleeblatt J, Betzler F, Kilarski L L, Bschor T, Köhler S. *Efficacy of off-label augmentation in unipolar depression: A systematic review of the evidence*. Eur Neuropsychopharmacol. 2017 Mar. 16. pii: S0924-977X(17)30185-2.

Pae 2014: Pae C U. *Pramipexole augmentation in treatment-resistant major depressive disorder*. Expert Rev Neurother. 2014 January; 14(1):5-8.

Piercey 1998: Piercey M F. *Pharmacology of pramipexole, a dopamine D3-preferring agonist, useful in treating Parkinson's disease*. ClinNeuropharmacol 1998; 21:141-151.

Poon et al. 2013: Poon S, Sim K, Baldessarini R J. *Pharmacological Approaches for Treatment-resistant Bipolar Disorder*. Curr Neuropharmacol. 2015; 13(5):592 604.

Schneider C S and Mierau J, 1987: Schneider C S, Mierau J "*Dopamine autoreceptor agonists: resolution and pharmacological activity of* 2,6-*diaminotetrahydrobenzothiazole and an aminothiazole analogue of apomorphine*"; J. Med Chem. 1987 March; 30(3):494-8.

Sienaert et al 2013: Sienaert P, Lambrichts L, Dols A, De Fruyt J. *Evidence-based treatment strategies for treatment-resistant bipolar depression: a systematic review*. Bipolar Disord. 2013 February; 15(1):61-9.

Tondo et al 2014: Tondo L, Vázquez G H, Baldessarini R J. *Options for pharmacological treatment of refractory bipolar depression*. Curr Psychiatry Rep. 2014 February; 16(2):431.

Willner et al. 1994: Willner P, Lappas S, Cheeta S, Muscat R. *Reversal of stress induced anhedonia by the dopamine agonist, pramipexole*. Psychopharmacol 1994; 115:454-462.

What is claimed is:

1. A method for treating a patient suffering from major depressive disorder (MDD), comprising orally administering to the patient a daily dose of 6 mg to 32 mg of ondansetron, or a pharmaceutically acceptable salt or solvate thereof and a daily dose of 0.125 mg to 20 mg of pramipexole, or a pharmaceutically acceptable salt or solvate thereof.

2. The method of claim 1, comprising administering to the patient a daily dose of about 0.125 mg to about 6 mg of pramipexole, or a pharmaceutically acceptable salt or solvate thereof.

3. The method of claim 1, comprising administering to the patient a daily dose of about 0.375 mg to about 6 mg of pramipexole, or a pharmaceutically acceptable salt or solvate thereof.

4. The method of claim 1, wherein the pramipexole is pramipexole dihydrochloride monohydrate.

5. The method of claim 4, comprising administering to the patient a daily dose of about 0.125 mg to about 6 mg of pramipexole dihydrochloride monohydrate.

6. The method of claim 4, comprising administering to the patient a daily dose of about 0.375 mg to about 6 mg of pramipexole dihydrochloride monohydrate.

7. The method of claim 4, comprising administering to the patient a daily dose of about 1 mg pramipexole dihydrochloride monohydrate.

8. The method of claim 4, comprising administering to the patient a daily dose of about 1.5 mg pramipexole dihydrochloride monohydrate.

9. The method of claim 4, comprising administering to the patient a daily dose of about 2.0 mg pramipexole dihydrochloride monohydrate.

10. The method of claim 4, comprising administering to the patient a daily dose of about 2.5 mg pramipexole dihydrochloride monohydrate.

11. The method of claim 4, comprising administering to the patient a daily dose of about 3.0 mg pramipexole dihydrochloride monohydrate.

12. The method of claim 4, comprising administering to the patient a daily dose of about 4.0 mg pramipexole dihydrochloride monohydrate.

13. The method of claim 4, comprising administering to the patient a daily dose of about 4.5 mg pramipexole dihydrochloride monohydrate.

14. The method of claim 1, wherein ondansetron is ondansetron hydrochloride dihydrate.

15. The method of claim 4, comprising administering to the patient a daily dose of about 0.125 mg to about 5 mg pramipexole dihydrochloride monohydrate.

16. The method of claim 4, comprising administering to the patient a daily dose of about 0.125 mg to about 4.5 mg pramipexole dihydrochloride monohydrate.

17. The method of claim 4, comprising administering to the patient a daily dose of about 0.125 mg to about 4 mg pramipexole dihydrochloride monohydrate.

18. The method of claim 4, comprising administering to the patient a daily dose of about 0.125 mg to about 3 mg pramipexole dihydrochloride monohydrate.

19. The method of claim 4, comprising administering to the patient a daily dose of about 0.125 mg to about 2 mg pramipexole dihydrochloride monohydrate.

20. The method of claim 4, comprising administering to the patient a daily dose of about 0.125 mg to about 1.625 mg pramipexole dihydrochloride monohydrate.

21. The method of claim 4, comprising administering to the patient a daily dose of about 0.125 mg to about 1.5 mg pramipexole dihydrochloride monohydrate.

22. The method of claim 4, comprising administering to the patient a daily dose of about 0.125 mg to about 1 mg pramipexole dihydrochloride monohydrate.

23. The method of claim 4, comprising administering to the patient a daily dose of about 0.125 mg to about 0.75 mg pramipexole dihydrochloride monohydrate.

24. The method of claim 4, comprising administering to the patient a daily dose of about 0.125 mg to about 0.5 mg pramipexole dihydrochloride monohydrate.

25. The method of claim 4, comprising administering to the patient a daily dose of about 0.125 mg to about 0.375 mg pramipexole dihydrochloride monohydrate.

26. The method of claim 4, comprising administering to the patient a daily dose of about 0.125 mg to about 0.25 mg pramipexole dihydrochloride monohydrate.

27. The method of claim 14, comprising administering to the patient a daily dose of about 6 mg to about 16 mg ondansetron hydrochloride dihydrate.

28. The method of claim 14, comprising administering to the patient a daily dose of about 8 mg to about 16 mg ondansetron hydrochloride dihydrate.

* * * * *